United States Patent [19]
Katz et al.

[11] Patent Number: 6,107,068
[45] Date of Patent: Aug. 22, 2000

[54] COENZYME A DISULFIDE REDUCTASE, AND INHIBITORS THEREOF USEFUL AS ANTIMICROBIAL AGENTS

[75] Inventors: Leonard Katz, Wheeling, Ill.; Stephen B. Delcardayre, Los Gatos, Calif.; Julian E. Davies, Vancouver, Canada

[73] Assignee: The University of British Columbia, Vancouver, Canada

[21] Appl. No.: 08/886,886

[22] Filed: Jul. 2, 1997

Related U.S. Application Data

[63] Continuation-in-part of application No. PCT/US96/20017, Dec. 19, 1996.

[60] Provisional application No. 60/009,146, Dec. 22, 1995.

[51] Int. Cl.[7] .............................. C12N 9/02; C12N 15/00; C12Q 1/37; C07H 21/04

[52] U.S. Cl. .................... 435/189; 435/24.3; 435/320.1; 435/252.3; 435/6; 536/23.2

[58] Field of Search .................................. 536/23.2, 24.3, 536/24.32; 435/320.1, 252.3, 252.2, 189, 6

[56] References Cited

U.S. PATENT DOCUMENTS

| | | | |
|---|---|---|---|
| 5,200,313 | 4/1993 | Carrico | 435/6 |
| 5,384,242 | 1/1995 | Oakes | 435/6 |
| 5,582,985 | 12/1996 | Thompson | 435/6 |

OTHER PUBLICATIONS

Result #15 from Oligomer Search using instant SEQ ID No.:1 as the query term, Dec. 2, 1995.

Luba et al. Coenzyme A–disulfide reductase from *Staphylococcus aureus*: Evidence for asymmetric behavior on interaction with pyridine nucleotides. Biochemistry 38:2725–2737, Mar. 1999.

Bellamacina, "The nicotinamide dinucleotide binding motif: a comparison of nucleotide binding proteins", *The FASEB Journal*, (vol. 10) pp. 1257–1268 (1996).

Claiborne, et al., "Flavin–linked peroxide reductases: protein–sulfenic acids and the oxidative stress response", *Trends in Biochemical Sciences*, (vol. 17) pp. 183–186 (1992).

Fahey, et al., "Occurrence of Glutathione in Bacteria", *Journal of Bacteriology*, (vol. 133) pp. 1126–1129 (1978).

Fahey, et al., "Evolution of Glutathione Metabolism", *Advances in Enzymology and Related Areas of Molecular Biology*, ed. Alton Meister, John Wiley & Sons, Inc., pp. 1–53 (1991).

Newton, et al., "Low–Molecular–Weight Thiols in Streptomycetes and Their Potential Role as Antioxidants", *Journal of Bacteriology*, (vol. 175) pp. 2734–2742, (1993).

Newton, et al., "Distribution of Thiols in Microorganisms: Mycothiol is a Major Thiol in most actinomycetes", *Journal of Bacteriology*, (vol. 178) pp. 1990–1995, (1996).

(List continued on next page.)

Primary Examiner—Karen Cochrane Carlson
Assistant Examiner—Devesh Srivastava
Attorney, Agent, or Firm—Robins & Associates

[57] ABSTRACT

An isolated and purified Coenzyme A disulfide reductase (CoADR) is provided. Oligonucleotides encoding the CoADR, vectors and host cells containing such oligonucleotides are also provided. In addition, antibodies reactive with the CoADR are provided, as are methods of isolating the CoADR, producing recombinant CoADR, using CoADR for screening compounds for CoADR-modulating activity, and detecting organisms which produce CoADR a test sample. Methods for identifying a gene encoding a CoADR are also provided.

24 Claims, 12 Drawing Sheets

```
ATGCCCaAAATAGTCGTAGTCGGAGCAGTCGCTGGTGGTGCAACATGTGCCAGCCAAATTCGACGTTTAGATAAAGAAAGTGACATT
ATTATTTttGAAAAAGATCGTGATATGAGCTTTGCTAATTGTGCATTGCCTTATGTCATTGGCGAAGTTGtTGAAGATAGAAGATAT
GCTTTAGCGTATaCACCtGAAAAATTTTATGATAGAAAGCAAATTACAGTAAAAACTTATCATGAaGTTATTGCAATCAATGATGAA
AGACAAaCTGTATCTGTATTAAATAGAAAGACAAACGAACAAtTTGAAGAATCTTACGATAAACTCATTTTAAGCCCTGGTGCAAGT
GCAAATAGCCTTGGCTTtGAaAGTGATATTACATTCACACTTAGAAATTTAGAAGACACTGATGCTATCGATCAATTCATCAAAGCA
AATCAaGTTGATAAGTATTGGTTGTAGGTGCAGGTTATGTTTCATTAGAAGTtCTTGAAAATCTTaATGAACGTGGttTACACCCT
ACTtTAATTCATCGATCTGATAAGATAAATAAATTAATGGATGCCGACATGAATCAACCTATACTTGATGAATTAGATAAGCGGGAG
ATTCCATACCGTTTAAATGAGGAAATTAATGCTATCAATGGAAATGAAATTACATTTAAATCAGGAAAAGTTGAACATTACGATATG
ATTATTGAAGGTGTCGGTACTCACCCCAATTCAAAATTTATCGAAAGTTCAAATATCAAACTTGATCGAAAAGGTTTCATACCGGTA
AACGATAAATTTGAAACAAATGTTCCAAACATTTATGCAATAGGCGATATTGCAACATCACATTATCGACATGTCGATCTACCGGCT
AGTGTTCCTTTAGCTTGGGGCGCTCACCGTGCAGCAAGTATTGTTGCCGAACAAATTGCTGGAAATGACACTATTGAATTCAAAGGC
TTCTTAGGCAACAATATTGTGAAGTTCTTTGATTATACATTTGCGAGTGTCGGCGTTAAACCAAACGAACTAAAGCAATTTGACTAT
AAAATGGTAGAAGTCACTCAAGGTGCACACGCGAATTATTACCCAGGAAATTCCCCTTTACACTTAAGAGTATATTATGACACTTCA
AACCGTCAGATTTTAAGAGCAGCTGCAGTAGGAAAAGAAGGTGCAGATAAACGTATTGATGTACTATCGATGGCAATGATGAACCAG
CTAACTGTAgATGAGTTAACTGAGTTTGAAGTGGCTTATGCACCACCATATAGCCACCCTAAAGATTTAATCAATATGATTGGTTAC
AAAGCTAAAtAA
```

OTHER PUBLICATIONS

Sakuda, et al., "Structure of a Novel Disulfide of 2–(N–Acetylcysteinyl)amido–2–deoxy–α–D–glucopyranosyl–myo–inositol Produced by Steptomyces sp.", *Biosci. Biotech. Biochem.*, (vol. 58) pp. 1347–1348, (1994).

Shames, et al., "Purification and Characterization of Trypanothione Reductase from *Crithidia fasciculata*, a Newly Discovered Member of the Family of Disulfide–Containing Flavoprotein Reductases", *Biochemistry*, (vol. 25) pp. 3519–3526 (1986).

Spies, et al., "Thiols of intracellular pathogens: Identification of ovothio A in *Leishmania donovani* and structural analysis of a novel thiol from *Mycobacterium bovis*", *Eur. J. Biochem.* (vol. 224) pp. 203–213 (1994).

Swerdlow, et al., "Purification and Characterization of a *Bacillus megaterium* Disulfide Reductase Specific for Disulfides Containing Pantethine 4',4"–Disphosphate", *Journal of Bacteriology* (vol. 153) pp. 475–484 (1983).

G.L. Newton et al., *Glutathione: Metabolism and Physiological Functions*, CRC Press, Boca Raton, FL., (1990), pp. 69–77.

A.H. Fairlamb, "Novel Biochemical Pathways in Parasitic Protozoa", *Parasitology*, vol. 99s, (1989), pp. 93–112.

```
ATGCCCAAAATAGTCGTAGTCGGAGCAGTCGCTGGTGGTGCAACATGTGCCAGCCAAATTCGACGTTTAGATAAAGAAAGTGACATT
ATTATTttGAAAAAGATCGTGATATGAGCTTTGCTAATTGTGCCTTATGTCATTGGCGAAGTTGTTGAAGATAGAAGATAT
GCTTTAGCGTATaCACCtGAAAAATTTATGATAGAAGCAAATTACAGTGAaGTTATTGCAATCAATGATGAA
AGACAAaCTGTATCTGTATTAAATAGAAAGACAAACAAaTTGAAGAATCTTACGATAAACTCATTTAAGCCCTGCAAGT
GCAAATAGCCTTGGCTTtGAaAGTGATATATTACATTCACACTTAGAAATTTAGAAGACACTGATGCTATCGATCAATTCATCAAAGCA
AATCAaGTTGATAAAGTATTGGTTGTGTAGGTGCAGGTTATGTTTCATTAGAAGTtCTTGAAAATCTtaATGAACGTGGttTACACCCT
ACTtTAATTCATCGATCGATAAGAGGAAATAAATAATGCTATCAAATTCAATGAATCAACCTATACTTGATGAATTAGATAAGCGGGAG
ATTCCATACCGTTTAAATGAGGAACTCACCCGAATGAAATTAAATTATCGAAAGTTCAAATATCAAACTTGATCGAAAAGGTTCATACCGGTA
ATTATTGAAGGTGTCGGTACTGTTGAAACAAATGTTCCAAACATTTATCAATAGGCGATATGCAACATGATGATCTACCGCT
AACGATAAATTGAAAAATTGAAACAAATGTTCCAAACATTTATGCAAGTATTGTTGCCGAACAAATGCTGGAATGACACTATTGAATTCAAAGC
AGTGTTCCTTTAGCTTGGGCGCTCACCGTGCAGCAAGTATTGTTGCCGAGTGTGCGGCGTGTAAACCAAACGAACTAAAGCAATTGACTAT
TTCTTAGGCAACAATATTGTGAAGTTCTTTGATTATACATTGCGAGTGTGCGGCGTGTAAACCAAACGAACTAAAGCAATTGACTAT
AAAATGGTAGAAGTCACTCAAGGTGCACACGCGAATTATTACCCAGGAAATTCCCCTTTACACTTAAGAGTATATTATGACACTTCA
AACCGTCAGATTTTAAGACAGCAGCTGCAGTAGGAAAAGAAGGTGCAGATAAACGTATTGATGTACTATCGATGCAATGATGAACCAG
CTAACTGTAgATGAGTTAACTGAGTTTGAAGTTAATCAATATAGCCACCCTAAAGATTAATCAATATGATTGGTTAC
AAAGCTAAAtAA
```

```
ATGAATAAAATTATAATAGTCGGTGCAGTTGCTGGTGGTGCGACTTGTGCAAGTCAAATT      60
 M  N  K  I  I  I  V  G  A  V  A  G  G  A  T  C  A  S  Q  I      20

CGAAGATTAGATAAAGAGAGTGAAATCATTGTTTTTGAAAAAGATAGAGACATGAGCTTT     120
 R  R  L  D  K  E  S  E  I  I  V  F  E  K  D  R  D  M  S  F      40

GCTAATTGTGCATTACCTTATTATATTGGCAACGTTATCGAGGACCGTCGTAAAGTTTTA    180
 A  N  C  A  L  P  Y  Y  I  G  N  V  I  E  D  R  R  K  V  L      60

GCATACACGCCCAATCAATTTTATGACAAAAAGCAAATCACTGTAAAAACATACCATGAA    240
 A  Y  T  P  N  Q  F  Y  D  K  K  Q  I  T  V  K  T  Y  H  E      80

GTTATACAAATCAATGATGAGAGACAAACAGTTACTGTCTTAAATCATCAAACTAATCAA    300
 V  I  Q  I  N  D  E  R  Q  T  V  T  V  L  N  H  Q  T  N  Q     100

ACTTTTGAAGAAAGTTACGATACATTGATTTTAAGTCCTGGCGCATCTGCAAATCGATTA    360
 T  F  E  E  S  Y  D  T  L  I  L  S  P  G  A  S  A  N  R  L     120

AACACTCATAGTGATATCTCATTTACTGTGCGAAATCTCGAAGATACTGAAACAATTGAT    420
 N  T  H  S  D  I  S  F  T  V  R  N  L  E  D  T  E  T  I  D     140

ACCTTTATTACGAATACCAAAGCACAACGTGCACTTGTTGTTGGCGCGGGTTACATCTCT    480
 T  F  I  T  N  T  K  A  Q  R  A  L  V  V  G  A  G  Y  I  S     160

TTAGAAGTCCTTGAAAATTTACATCATAGAGGTTTGGATGTCACATGGATTCATCGCTCT    540
 L  E  V  L  E  N  L  H  H  R  G  L  D  V  T  W  I  H  R  S     180

ACAAATATTAATAAACTGATGGATCAAGATATGAATCAACCCATCATCGACGAAATAGAA    600
 T  N  I  N  K  L  M  D  Q  D  M  N  Q  P  I  I  D  E  I  E     200

AAGAGAAATATCACTTATAGATTTAACGAAGAAATTAGTCACGTAAATGGACATGAAGTT    660
 K  R  N  I  T  Y  R  F  N  E  E  I  S  H  V  N  G  H  E  V     220

ACATTCACATCTGGTAAAGTTGAAAACTTTGATCTTATTATCGAAGGTGTAGGTACTCAT    720
 T  F  T  S  G  K  V  E  N  F  D  L  I  I  E  G  V  G  T  H     240

CCAAATTCACAATTTATTAAATCATCTAACGTCATACTGAATGATAAAGGTTATATCCCA    780
 P  N  S  Q  F  I  K  S  S  N  V  I  L  N  D  K  G  Y  I  P     260

GTAAATCATAATTTCCAAACAAATATACCAAATATTTATGCATTAGGTGATGTTATTACT    840
 V  N  H  N  F  Q  T  N  I  P  N  I  Y  A  L  G  D  V  I  T     280

TCACATTATCGTCATGTGAATTTACCGGCACAGGTTCCACTTGCTTGGGGAGCACACCGT    900
 S  H  Y  R  H  V  N  L  P  A  Q  V  P  L  A  W  G  A  H  R     300

GGTGCAAGTATTATAGCTGAACAACTTTCTGGAAATTCGTCTATTCACTTTAAAGGTTAT    960
 G  A  S  I  I  A  E  Q  L  S  G  N  S  S  I  H  F  K  G  Y     320

CTAGGAAATAATATAGTGAAATTTTTTGACTATACATTAGCAAGTGTTGGCATCAAACCA   1020
 L  G  N  N  I  V  K  F  F  D  Y  T  L  A  S  V  G  I  K  P     340

AATGAACTTAAAAATTTCGATTATGATATGGTTGAAGTTAAGCAAGGAGCTCATGCAGGA   1080
 N  E  L  K  N  F  D  Y  D  M  V  E  V  K  Q  G  A  H  A  G     360
```

Figure 3(b)

```
TATTACCCAGGAAATTCACCACTACATTTACGTGTTTATTTTGAAAAAGACTCGAGAAAA      1140
 Y  Y  P  G  N  S  P  L  H  L  R  V  Y  F  E  K  D  S  R  K        380

CTTATACGCGCAGCAGCAGTTGGTAAACAAGGTGCCGATAAAAGAATAGACGTATTATCA      1200
 L  I  R  A  A  A  V  G  K  Q  G  A  D  K  R  I  D  V  L  S        400

ATGGCAATGATGAATAATGCTACTGTGGATGATTTAACAGAATTTGAAGTAGCATATGCA      1260
 M  A  M  M  N  N  A  T  V  D  D  L  T  E  F  E  V  A  Y  A        420

CCTCCTTATAGTCATCCAAAAGATTTAATTAATTTAATTGGGTATAAAGCGCAATAA        1317
 P  P  Y  S  H  P  K  D  L  I  N  L  I  G  Y  K  A  Q  *           438
```

Figure 4(a)

```
ATGAAAATTGTAATTATCGGAGGCGTGGCTGGTGGTATGTCAGCAGCGACACGTTTACGT      60
 M  K  I  V  I  I  G  G  V  A  G  G  M  S  A  A  T  R  L  R        20

CGTTTAATGGAAGATGCTGAAATTGTTGTCATGGAAAAAGGCCCTTTTGTTTCATTTGCA     120
 R  L  M  E  D  A  E  I  V  V  M  E  K  G  P  F  V  S  F  A        40

AACTGTGGTTTGACTTACTACGTTTCTGGCGAAATCGCAGAAAGAGAGCAACTGCTTGTT     180
 N  C  G  L  T  Y  Y  V  S  G  E  I  A  E  R  E  Q  L  L  V        60

CAAACACCCGAAGCGTTAAAGGCACGGTTTAATTTAGATGTTCGTCCTCACCATGAAGTC     240
 Q  T  P  E  A  L  K  A  R  F  N  L  D  V  R  P  H  H  E  V        80

GTGGCGATTGATCCAATAGAAAAGTGATCACAGTGAAACATGAAACAGAAATTTTAACA     300
 V  A  I  D  P  I  E  K  V  I  T  V  K  H  E  T  E  I  L  T       100

GAACACTATGACAAATTAATTTTATCACCAGGGGCGAAACCTTTTGTGCCACCAATTACA     360
 E  H  Y  D  K  L  I  L  S  P  G  A  K  P  F  V  P  P  I  T       120

GGATTGGCAGAAGCCAAAAATGTTTTTTCATTAAGAAATGTTCCTGATTTAGATCAAATT     420
 G  L  A  E  A  K  N  V  F  S  L  R  N  V  P  D  L  D  Q  I       140

ATGACAGCCTTGACACCAGAAACAAAACGAGCCGTCGTGATTGGCGCAGGCTTCATTGGC     480
 M  T  A  L  T  P  E  T  K  R  A  V  V  I  G  A  G  F  I  G       160

TTGGAAATGGCAGAAAACTTGCAAAAACGCGGATTAGAAGTCACTCTCGTGGAAAAAGCG     540
 L  E  M  A  E  N  L  Q  K  R  G  L  E  V  T  L  V  E  K  A       180

CCTCATGTTTTACCGCCATTAGACGAAGAAATGGCCGCTTTTGTCAAAGCTGAATTAAGC     600
 P  H  V  L  P  P  L  D  E  E  M  A  A  F  V  K  A  E  L  S       200

AAAAACAATGTTCAAGTAATTACGGGACAATCTGCGGTTGCTTTTGAAGAAGAAGGGCAA     660
 K  N  N  V  Q  V  I  T  G  Q  S  A  V  A  F  E  E  E  G  Q       220

GTGATTCGCTTAGAAGACGGTCAAACATTAGCTTCTGATTTAACCATTTTGTCGGTGGGT     720
 V  I  R  L  E  D  G  Q  T  L  A  S  D  L  T  I  L  S  V  G       240

GTCCAACCAGAAAATACCTTAGCAGTTGAAGCAGGTGTAGCAACTGGTTTACGTGGCGGT     780
 V  Q  P  E  N  T  L  A  V  E  A  G  V  A  T  G  L  R  G  G       260

ATTGTTGTTGATGAACACTATCAAACGAATCAACCCGATATTTATGCGGTTGGGGATGCT     840
 I  V  V  D  E  H  Y  Q  T  N  Q  P  D  I  Y  A  V  G  D  A       280

GTTGTAGTGAAACAACAAATCACTCAAGAAGATGCGCTGATTTCTTTAGCTTCTCCTGCC     900
 V  V  V  K  Q  Q  I  T  Q  E  D  A  L  I  S  L  A  S  P  A       300

AATCGCCAAGGACGTCAAGTAGCGGATGTGATTGCTGGGTTAGAGAGAAAAAATCAAGGA     960
 N  R  Q  G  R  Q  V  A  D  V  I  A  G  L  E  R  K  N  Q  G       320

AGCATTGGGACTGCCATTGTGCGAGTCTTTGATTTAACCGCTGCTTCAACTGGTTTAAGC    1020
 S  I  G  T  A  I  V  R  V  F  D  L  T  A  A  S  T  G  L  S       340

GAACGGGCTGCTAAAGCTGCTGGACTAACAACAGCTGTTGTGCATATCAGTGGAAAAGAC    1080
 E  R  A  A  K  A  A  G  L  T  T  A  V  V  H  I  S  G  K  D       360
```

Figure 4(b)

```
CATGCGGGGTATTATCCTGGCGCAACAGATCTTCAGTTAAAATTAGTTTTTCATCCTACG    1140
H   A   G   Y   Y   P   G   A   T   D   L   Q   L   K   L   V   F   H   P   T      380

ACAGGGGAAATTTATGGCGCACAAGGAATTGGGGCAAAGGGCGTAGATAAGCGGATTGAT    1200
T   G   E   I   Y   G   A   Q   G   I   G   A   K   G   V   D   K   R   I   D      400

ATTCTTGCGACCGCTATTAAAGGACAGTTAACTATTTTTGATTTGCCTGAATTAGAGTTT    1260
I   L   A   T   A   I   K   G   Q   L   T   I   F   D   L   P   E   L   E   F      420

ACCTATGCCGCCGTTTGGTTCAGCGAAAGATCCTGTGAACATGTTAGGCTATGCAGCG     1320
T   Y   A   P   P   F   G   S   A   K   D   P   V   N   M   L   G   Y   A   A      440

ATGAACCTTGCAGAAGGATTGAGTGAAAACATTCAATGGTATGAGCTATCCAACGAATTA    1380
M   N   L   A   E   G   L   S   E   N   I   Q   W   Y   E   L   S   N   E   L      460

GCTAATGGGGCTGTTTTATTAGATGTCCGTAATCCCGCCGAACGAGCCAATGGTCAATTT    1440
A   N   G   A   V   L   L   D   V   R   N   P   A   E   R   A   N   G   Q   F      480

AAAAATGCTGTGTCTATTCCTTTAAATGAGTTAAGAGAACGTTTGGAGGAATTAGACAAG    1500
K   N   A   V   S   I   P   L   N   E   L   R   E   R   L   E   E   L   D   K      500

TCAACGGAGTACATTGTTAGTTGTCACAGCGGTTTGCGTAGTTATATTGCAGAACGGATG    1560
S   T   E   Y   I   V   S   C   H   S   G   L   R   S   Y   I   A   E   R   M      520

CTAAAACAAGCGGGCATCTCAGCCAAAAATTTAGATGGTGCTTTTGCGCTATATCGAATG    1620
L   K   Q   A   G   I   S   A   K   N   L   D   G   A   F   A   L   Y   R   M      540

GTAAAATCGGAGGAACTAGAAAATGTATAA                                  1650
V   K   S   E   E   L   E   N   V   *                            550
```

Figure 5(a)

```
ATGAAAATCGTTATTGTCGGAGGTGTAGCAGGTGGAATGTCTGCTGCTACACGGCTTCGC      60
 M   K   I   V   I   V   G   G   V   A   G   G   M   S   A   A   T   R   L   R       20

CGATTAATGGAAGATGCAGAAATCGTTGTTTTTGAAAAAGGACCGTATGTTTCTTTTGCA     120
 R   L   M   E   D   A   E   I   V   V   F   E   K   G   P   Y   V   S   F   A       40

AATTGCGGCTTGCCTTATTATCTTTCGGGAGAAATCAGTGAACGGGAAAATCTTCTTGTC     180
 N   C   G   L   P   Y   Y   L   S   G   E   I   S   E   R   E   N   L   L   V       60

CAAACGCCAGAATCATTATCCGCTCGTTTTTGTTTAGATGTGCGTCCAAATCATGAAGTG     240
 Q   T   P   E   S   L   S   A   R   F   C   L   D   V   R   P   N   H   E   V       80

ACAGCCATCTTTCCCGAAAACAAAACGGTAGAAGTCGTACATGAGGGTCAAAAACACATT     300
 T   A   I   F   P   E   N   K   T   V   E   V   V   H   E   G   Q   K   H   I      100

GAACAGTACGATGCATTGGTTTTATCTCCTGGTGCAAAACCAGTTGTTCCATCGATTCCA     360
 E   Q   Y   D   A   L   V   L   S   P   G   A   K   P   V   V   P   S   I   P      120

GGGATAACAGAAGCCGACAATGTTTTTTCTATTAGAAATGTACCAGATATCGATAAAGTG     420
 G   I   T   E   A   D   N   V   F   S   I   R   N   V   P   D   I   D   K   V      140

ATACATGCATTAGAAAAACAGCCAAAGCGTGCCGTGATCGTTGGTGCAGGATTCATCGGA     480
 I   H   A   L   E   K   Q   P   K   R   A   V   I   V   G   A   G   F   I   G      160

TTGGAAATGGCAGAAAACCTAAAAAGAAGAGGTTTAGAAGTCATGGTGATCGAACAAGCA     540
 L   E   M   A   E   N   L   K   R   R   G   L   E   V   M   V   I   E   Q   A      180

CCACATATTCTTCCGACGCTGGATGAAGAAATGGCAGCTTTTATAGAAAAAGAATTGTCT     600
 P   H   I   L   P   T   L   D   E   E   M   A   A   F   I   E   K   E   L   S      200

CATCAAGGAGTAGAAGTGATTACTTCTCATGCTGTCGCTGGATTTGAAGACCACGGGAAA     660
 H   Q   G   V   E   V   I   T   S   H   A   V   A   G   F   E   D   H   G   K      220

CGATTGCGACTGGATGATGGGCGTACCATCCCTGCTGATTTAGTTATTTTATCCATTGGT     720
 R   L   R   L   D   D   G   R   T   I   P   A   D   L   V   I   L   S   I   G      240

GTTCGTCCTGATAACCAGCTAGCAGTGACTGCTGGAATCGAATTAGGTATACGCGGGGGT     780
 V   R   P   D   N   Q   L   A   V   T   A   G   I   E   L   G   I   R   G   G      260

ATCCTAGTAGACGAACGATATCAAACGAATATTCCTGATATTTATGCGGTGGGGGATGCT     840
 I   L   V   D   E   R   Y   Q   T   N   I   P   D   I   Y   A   V   G   D   A      280

ATCGTTGTAAAACAGCAAATCACTGGAAAAGATGCACTTATTTCTCTTGCTTCACCAGCC     900
 I   V   V   K   Q   Q   I   T   G   K   D   A   L   I   S   L   A   S   P   A      300

AATCGTCAAGGTAGACAAGTTGCGGACACGATTTCCGGAATTTCTCGAAGAAATCAAGGC     960
 N   R   Q   G   R   Q   V   A   D   T   I   S   G   I   S   R   R   N   Q   G      320

GGTATTGGAACAGCAATTATACGAACGTTTGGAATGACTGCCGCATCCACCGGTTTAAGT    1020
 G   I   G   T   A   I   I   R   T   F   G   M   T   A   A   S   T   G   L   S      340

GAAAGAACAGCCAAAGAAAACGAACTGTCTTTTGAAGTCATTCATGTATCAGGAAAAGAT    1080
 E   R   T   A   K   E   N   E   L   S   F   E   V   I   H   V   S   G   K   D      360
```

Figure 5(b)

```
CATGCAAGCTATTATCCAGAAGCAACAGATATTTTACTGAAGTTGATCTTCCATCCAGAG    1140
 H  A  S  Y  Y  P  E  A  T  D  I  L  L  K  L  I  F  H  P  E      380

ACTGGCGAGATTTATGGTGCACAAGGTGTTGGGGCAAAAGGTGTGGATAAACGGATCGAT    1200
 T  G  E  I  Y  G  A  Q  G  V  G  A  K  G  V  D  K  R  I  D      400

ATTTTAGCAACAGCAATCAAAGGGCATTTGACGATCTTCGATTTACCGGAATTAGAATTG    1260
 I  L  A  T  A  I  K  G  H  L  T  I  F  D  L  P  E  L  E  L      420

ACGTATGCACCGCCATTTGGCTCAGCCAAAGATCCAGTAAACATGCTAGGATATGCAGCA    1320
 T  Y  A  P  P  F  G  S  A  K  D  P  V  N  M  L  G  Y  A  A      440

ATGAACATTGTAGAAGGGCTTAGTGAAACCGTACAATGGCATGAATTGCCGACAGAATTA    1380
 M  N  I  V  E  G  L  S  E  T  V  Q  W  H  E  L  P  T  E  L      460

GCAAAAGGAAAAATTTTATTAGATGTGCGAACAGCAGAAGAATTGGAAAAAGGCAAATTC    1440
 A  K  G  K  I  L  L  D  V  R  T  A  E  E  L  E  K  G  K  F      480

AAGGAAGCCAAACATATCCCTTTGAATGAACTTCGAGACCGATTAGATGAATTAGACAGC    1500
 K  E  A  K  H  I  P  L  N  E  L  R  D  R  L  D  E  L  D  S      500

CAGCAAGAATATATCGTCAGCTGTCATAGTGGGCTACGTAGCTATCTAGCGGAAAGAATC    1560
 Q  Q  E  Y  I  V  S  C  H  S  G  L  R  S  Y  L  A  E  R  I      520

TTGAAGCAGTCTGGCTACCACGTAAAAAACCTTGATGGTGCATTTTCTTTATATCAAACT    1620
 L  K  Q  S  G  Y  H  V  K  N  L  D  G  A  F  S  L  Y  Q  T      540

GTCCGACAAGAAGAACTGATATATCCTAACAAATGA                            1656
 V  R  Q  E  E  L  I  Y  P  N  K  *                              552
```

Figure 6(a)

```
ATGAAAGTTGTTGTCATTGGCGGTGTAGCTGGCGGTCCTTCATTTGCCACTCGTTTCCGT    60
 M   K   V   V   V   I   G   G   V   A   G   G   P   S   F   A   T   R   F   R    20

CGATTGAATGAAGCACACGAAATCATTATCTATGAACGCGGAGAGAATATTTCTTACGCA   120
 R   L   N   E   A   H   E   I   I   I   Y   E   R   G   E   N   I   S   Y   A    40

AGTTGTGCTTTGCCTTATTATTTAGGTGGTGTGATCACGGACCGTGACTCGCTGATCGAA   180
 S   C   A   L   P   Y   Y   L   G   G   V   I   T   D   R   D   S   L   I   E    60

CGTACACCAGAAATATTGAAAACAAAAAACAACATCGACGTATTTACTAAACACGAAGTA   240
 R   T   P   E   I   L   K   T   K   N   N   I   D   V   F   T   K   H   E   V    80

ACAGCAATCGATCCTTCTACTAAGCGATTAACAGTTAAAGACCTATCCACAAATGAAGAA   300
 T   A   I   D   P   S   T   K   R   L   T   V   K   D   L   S   T   N   E   E   100

ACAAAAACAGATTACGATAAGTTGATCATCTCTTCTGGTGCTAGACCAGATTATCCGGAT   360
 T   K   T   D   Y   D   K   L   I   I   S   S   G   A   R   P   D   Y   P   D   120

ATTCCCGGAGTTTTTGAAGCAGAAAACGGCTTTGTACTCCGTAGTGTGACGGATGCGGAT   420
 I   P   G   V   F   E   A   E   N   G   F   V   L   R   S   V   T   D   A   D   140

CGAATCAAATCGTTCCTTGAAGAAAAAAATCCACAACATGTCGTCATTCTTGGTGCAGGT   480
 R   I   K   S   F   L   E   E   K   N   P   Q   H   V   V   I   L   G   A   G   160

GTTATGGGTCTGGAATTAGCTGAGAATCTCAAGCATCGCGGCTTAAACGTGACTTTAATC   540
 V   M   G   L   E   L   A   E   N   L   K   H   R   G   L   N   V   T   L   I   180

GATCAATTGCCACAAGTCGCTTTCCCTTATGATCCAGAAATTGCTAATTTAGTTTATGAC   600
 D   Q   L   P   Q   V   A   F   P   Y   D   P   E   I   A   N   L   V   Y   D   200

AAATTGCTGAAAGAAGGATTAGCCGTTCATTTAGAAACAAGAGTTACTGAGATCCGTGAT   660
 K   L   L   K   E   G   L   A   V   H   L   E   T   R   V   T   E   I   R   D   220

AAAGGTCGAGAAATAATATTATCAGATGGTTCCGTCCTTTCTGCTGATATGCTAATTTTT   720
 K   G   R   E   I   I   L   S   D   G   S   V   L   S   A   D   M   L   I   F   240

GCTGTTGGTGTTTCTCCGAATAATGAAGTGGTGAAAGCAGCCGGCATAAAATTATCTGAT   780
 A   V   G   V   S   P   N   N   E   V   V   K   A   A   G   I   K   L   S   D   260

ACAGGACAGATCATTGTCGATGACCAGTTACAAACCAATCTTCCGGACATCTATGCGATT   840
 T   G   Q   I   I   V   D   D   Q   L   Q   T   N   L   P   D   I   Y   A   I   280

GGCGATATTATCGAAACAACTAGTGTAGTGACTGGTCAGCCGATCCAAAGTATGCTTTCC   900
 G   D   I   I   E   T   T   S   V   V   T   G   Q   P   I   Q   S   M   L   S   300

AGTGCGGCCAATCGTCAAGGACACATGTTGGCAGATATTTTAAATGGTACGCCTATGCGC   960
 S   A   A   N   R   Q   G   H   M   L   A   D   I   L   N   G   T   P   M   R   320

TATCGCGGATATATTGGTGCAGGTGTCGCAAAAATCTTTGATCATACAGCAAGTTATGCT  1020
 Y   R   G   Y   I   G   A   G   V   A   K   I   F   D   H   T   A   S   Y   A   340

GGAATGACAGAACATGCACTAAAAGCATCAGGCATAACAAATTATAAAACTGTTTTTATC  1080
 G   M   T   E   H   A   L   K   A   S   G   I   T   N   Y   K   T   V   F   I   360
```

Figure 6(b)

```
ACTCCTTTTGACCATGCCTATTTCTATCCAGGAGCTACAAGATTAAATCTAAAGCTGATT    1140
 T  P  F  D  H  A  Y  F  Y  P  G  A  T  R  L  N  L  K  L  I      380

TTTGATGCAGATAGCGGTCGTATTTTAGGTGGACAAGCATTTGGAGAAAAAGGTGTCGAT    1200
 F  D  A  D  S  G  R  I  L  G  G  Q  A  F  G  E  K  G  V  D      400

AAACGGATGGGAGAACTTTCTGTAGCGATCACCGGAAACTTGACAGTCTTTGATTTGCCC    1260
 K  R  M  G  E  L  S  V  A  I  T  G  N  L  T  V  F  D  L  P      420

GATTTGGAGTTGCCTTACTCTCCACCGTATTCTACTACCCGTGATCCGTTGAATATAGCT    1320
 D  L  E  L  P  Y  S  P  P  Y  S  T  T  R  D  P  L  N  I  A      440

GGTTATGTCGCAATCAATCAAATGACGAATATCGTAGAAACGATCAAAGCAAGTGATATA    1380
 G  Y  V  A  I  N  Q  M  T  N  I  V  E  T  I  K  A  S  D  I      460

CCCGAAAACGATTTGAAAGAAGCGTTCTTTTTAGACATACGTGAACCTAATAAAGCACCT    1440
 P  E  N  D  L  K  E  A  F  F  L  D  I  R  E  P  N  K  A  P      480

CCCGAAAACGATTTGAAAGAAGCGTTCTTTTTAGACATACGTGAACCTAATAAAGCACCT    1500
 S  G  S  I  S  A  T  K  N  I  P  M  N  E  L  R  D  R  I  N      500

GAAATCCCAAAAGATAAAAAAATTTATATTACTTTCAGAAGAGGATTGAATACTTATACT    1560
 E  I  P  K  D  K  K  I  Y  I  T  F  R  R  G  L  N  T  Y  T      520

TCTGCCCGAATCTTGGCAGGTTTGGGTATCAAAGCGGTTTTGATTGAAGAATAA          1614
 S  A  R  I  L  A  G  L  G  I  K  A  V  L  I  E  E  *            538
```

Figure 7(a)

```
                   1                                                                                              60
       Cdr_Se   MnKIiivGaV  AGGatcAsqi  RRLdkesEIi  vfEKdrdmSF  ANCaLPYYig  nvIedRrkvL
       Cdr_Sa   MpKIVvvGaV  AGGatcAsqi  RRLdkesdIi  ifEKdrdmSF  ANCaLPYvig  evvedRryaL
       Cdr_Efa  M KIViiGgV  AGGmsaAtrl  RRLmedaEIv  vmEKgpfvSF  ANCgLtYYvs  geIaeReqlL
       CdrA_Efm M KIVivGgV  AGGmsaAtrl  RRLmedaEIv  vfEKgpyvSF  ANCgLPYYls  geIseRenlL
       CdrB_Efm M KvVviGgV  AGGpsfAtrf  RRLneahEIi  iyErgeniSy  AsCaLPYYlg  gvItdRdsli
       Consensus M-KIV--G-V AGG---A---  RRL----EI-  --EK----SF  ANC-LPYY--  --I--R---L 120
       Cdr_Se   ayTPnqfydk  kqitVktyHE  ViqInderqt  vtVlnhqtnq  tfeEsYDtLI  LSPGAsanrl
       Cdr_Sa   ayTPEkfydr  kqitVktyHE  ViAInderqt  vsVlnrktne  qfeEsYDkLI  LSPGAsansl
       Cdr_Efa  vqTPEalkar  fnldVrphHE  VvAIdpiekv  itVk..hete  iltEhYDkLI  LSPGAkpfvp
       CdrA_Efm vqTPEslsar  fcldVrpnHE  VtAIfpenkt  veVv..hegq  khiEqYDaLv  LSPGAkpvvp
       CdrB_Efm erTPEilktk  nnidVftkHE  VtAIdpstkr  ltVkdlstne  etktdYDkLI  iSsGArpdyp
       Consensus --TPE-----  ----V---HE  V-AI------  --V-------  ---E-YD-LI  LSPGA-----

180
       Cdr_Se   n....thsdi  sFtvRNleDt  etIdtfitnt  kaqralvvGA  GyisLEvlEN  LhhRGLdVTw
       Cdr_Sa   g....fEsdi  tFtlRNleDt  DaIdqfikan  qvdkvlvvGA  GyvsLEvlEN  LneRGLhpTl
       Cdr_Efa  pitglaEakn  vFslRNvpDl  DqImtal.tp  etkravviGA  GfigLEmaEN  LqkRGLeVTl
       CdrA_Efm sipgitEadn  vFsiRNvpDi  Dkvihal.ek  qpkravivGA  GfigLEmaEN  LkrRGLeVmv
       CdrB_Efm dipgvfEaen  gFvlRsvtDa  DrIksfleek  npqhvvilGA  GvmgLElaEN  LkhRGLnVTl
       Consensus ------E---  -F--RN--D-  D-I-------  --------GA  G---LE--EN  L--RGL-VT- 240
       Cdr_Se   Ihrstninkl  mDqdMnqpii  dEieKrnity  rfneeishv.  .nGhevtfts  GkvenfDliI
       Cdr_Sa   Ihrsdkinkl  mDadMnqpil  dELdKreipy  rlneeinai.  .nGneitfks  GkvehyDmiI
       Cdr_Efa  vekaphvlpp  lDeeMaafvk  aELsKnnvqv  itgqsavafe  eeGqvirled  GqtlasDltI
       CdrA_Efm Ieqaphilpt  lDeeMaafie  kELshqgvev  itshavagfe  dhGkrlrldd  GrtipaDlvI
       CdrB_Efm Idqlpqvafp  yDpeianlvy  dkLlKeglav  hletrvteir  dkGreiilsd  GsvlsaDmlI
       Consensus I---------  -D--M-----  -EL-K-----  ----------  --G-------  G-----D--I 300
       Cdr_Se   egVGthPnsq  fikssnviLn  dkGyIpVnhn  fQTNiPnIYA  lGDvitshyr  hvnlpAqvpL
       Cdr_Sa   egVGthPnsk  fiessnikLd  rkGfIpVndk  feTNvPnIYA  iGDiatshyr  hvdlpAsvpL
       Cdr_Efa  lsVGvqPent  laveagvatg  lrGgIvVdeh  yQTNqPdIYA  vGDavvvkqq  itqedAlisL
       CdrA_Efm lsiGvrPdnq  lavtagieLg  irGgIlVder  yQTNiPdIYA  vGDaivvkqq  itgkdAlisL
       CdrB_Efm faVGvsPnne  vvkaagikLs  dtGqIiVddq  lQTNlPdIYA  iGDiiettsv  vtgqpiqsmL
       Consensus --VG--P---  --------L-  --G-I-V---  -QTN-P-IYA  -GD-------  -----A---L 360
       Cdr_Se   AwgAhRgasi  iAeqlsGnss  ihfkGylGnn  IvkfFDyTlA  SvGikpnelK  n...fdydmV
       Cdr_Sa   AwgAhRaasi  vAeqiaGndt  iefkGflGnn  IvkfFDyTfA  SvGvkpnelK  q...fdykmV
       Cdr_Efa  AspAnRqgrq  vAdviaGler  .knqGsiGta  IvrvFDlTaA  StGlseraaK  aaglt.tavV
       CdrA_Efm AspAnRqgrq  vAdtisGisr  .rnqGgiGta  IirtFgmTaA  StGlsertaK  enels.fevi
       CdrB_Efm ssaAnRqghm  lAdilnGtpm  .ryrGyiGag  vakiFDhTas  yaGmtehalK  asgitnyktV
       Consensus A--A-R----  -A----G---  ----G--G--  I---FD-T-A  S-G------K  ---------V
```

Figure 7(b)

```
                                                                                           420
   Cdr_Se  evkqgaHAgY  YPGnspLhLr  vyFekdsrkl  irAaavGkqG  aDKRIDvLsm  AmmnnaTvdD
   Cdr_Sa  evtqgaHAnY  YPGnspLhLr  vyydtsnrqI  lrAaavGkeG  aDKRIDvLsm  AmmnqLTvde
   Cdr_Efa hisgkdHAgY  YPGatdLqLk  lvFhpttgeI  ygAqgiGakG  vDKRIDiLat  AikgqLTifD
  CdrA_Efm hvsgkdHAsY  YPeatdilLk  liFhpetgeI  ygAqgvGakG  vDKRIDiLat  AikghLTifD
  CdrB_Efm fitpfdHAyf  YPGatrLnLk  liFdadsgrI  lggqafGekG  vDKRmgeLsv  AitgnLTvfD
 Consensus ------HA-Y  YPG---L-L-  --F------I  --A---G--G  -DKRID-L--  A----LT--D 480
   Cdr_Se  LtEfEvaYAP  PyshpKDliN  liGYkAq*~~  ~~~~~~~~~~  ~~~~~~~~~~  ~~~~~~~~~~
   Cdr_Sa  LtEfEvaYAP  PyshpKDliN  miGYkAk*~~  ~~~~~~~~~~  ~~~~~~~~~~  ~~~~~~~~~~
   Cdr_Efa LpElEftYAP  PfgsaKDpvN  mlGYaAmnla  eglseniqwy  elsnelanga  vlldvrnpae
  CdrA_Efm LpElEltYAP  PfgsaKDpvN  mlGYaAmniv  eglsetvqwh  elptelakgk  illdvrtaee
  CdrB_Efm LpdlElpYsP  PysttrDplN  iaGYvAinqm  tnivetikas  dipendlkea  ffldirepnk
 Consensus L-E-E--YAP  P----KD--N  --GY-A-n--  ----e-i---  el--e-----  --ldvr----

540
   Cdr_Se  ~~~~~~~~~~  ~~~~~~~~~~  ~~~~~~~~~~  ~~~~~~~~~~  ~~~~~~~~~~  ~~~~~~~~~~
   Cdr_Sa  ~~~~~~~~~~  ~~~~~~~~~~  ~~~~~~~~~~  ~~~~~~~~~~  ~~~~~~~~~~  ~~~~~~~~~~
   Cdr_Efa rangqfknav  siplnelrer  leeldkstey  ivschsglrs  yiaermlkqa  gisaknldga
  CdrA_Efm lekgkfkeak  hiplnelrdr  ldeldsqqey  ivschsglrs  ylaerilkqs  gyhvknldga
  CdrB_Efm apsgsisatk  nipmnelrdr  ineipkdkki  yitfrrglnt  ytsarilagl  gikavliee*
 Consensus ---g------  --p---lrdr  l-el------  --s---gl-s  y---r-----  g---------

558
   Cdr_Se  ~~~~~~~~~~  ~~~~~~~~
   Cdr_Sa  ~~~~~~~~~~  ~~~~~~~~
   Cdr_Efa falyrmvkse  elenv*~~
  CdrA_Efm fslyqtvrqe  eliypnk*
  CdrB_Efm ~~~~~~~~~~  ~~~~~~~~
 Consensus ----------  --------
```

COENZYME A DISULFIDE REDUCTASE, AND INHIBITORS THEREOF USEFUL AS ANTIMICROBIAL AGENTS

CROSS-REFERENCE TO RELATED APPLICATIONS

This application is a continuation-in-part application of International Application No. PCT/US96/20017 filed Dec. 19, 1996 (now WO 9723628, Jul. 3, 1997) which claims the benefit of priority to U.S. Provisional Application Ser. No. 60/009,146, filed Dec. 22, 1995.

TECHNICAL FIELD

This invention relates generally to microbial metabolism and antimicrobial therapeutic agents. In particular, the invention relates to a novel enzyme that plays an important role in the metabolism of a number of microorganisms, including *Staphylococcus aureus*, to compounds that inhibit this enzyme, and to the use of these compounds as antimicrobial agents, particularly for the therapy of infections caused by Gram-positive organisms, especially Staphylococcus spp. and Enterococcus spp. infections.

BACKGROUND

Glutathione (GSH; g-glutamyl-cysteinyl-glycine) is the predominant thiol produced by aerobic eukaryotes and Gram-positive bacteria. It is believed to protect aerobic organisms from oxygen toxicity and to participate in a multitude of functions. GSH acts as a slowly autooxidizing reserve of cysteine and as a cofactor in the detoxification of peroxides, epoxides, and other products resulting from reaction with oxygen. It is a cofactor in the reduction of disulfides and ribonucleotides and in the isomerization of protein disulfides. Thiols are the most reactive nucleophiles in the cell at physiological pH, and when exposed to atmospheric oxygen are oxidized to disulfides (RSH/RSSR= $10^{-16}$). Glutathione reductase (GSR; E.C.1.6.4.2) catalyzes the NADPH-dependent reduction of intracellular oxidized glutathione (GSSG) and thereby maintains a reducing environment in the cell (GSH/GSSG>100). GSH was once thought to be ubiquitous. However, many organisms do not produce GSH but instead produce alternative thiols. Fahey et al. (1978) *J. Bacteriol.* 133:1126–1129; Fahey et al. (1991) in Meister (ed.) *Advances in Enzymology and Related Areas of Molecular Biology* 64:1–53 (John Wiley and Sons); Fairlamb (1989) *Parisitol.* 99S:93–112; Newton et al. (1989), in Vina (ed.), *Glutathione: Metabolism and Physiological Functions* pp. 69–77 (CRC Press, Boca Raton. Fla.); Newton et al. (1993) *J. Bacteriol.* 175:2734–2742; Sakuda et al. (1994) *Biosci. Biotechnol. Biochem.* 58:1347–1348; and Spies et al. (1994) *Eur. J. Biochem.* 224:203–213.

For example, *Staphylococcus aureus* produces Coenzyme A (CoA) as its major thiol instead of glutathione. Newton et al. (1996) *J. Bacteriol.*, in press. CoA is slightly more stable than glutathione to heavy metal-catalyzed auto-oxidation and provides a stable redox buffer similar to that provided by GSH in other organisms. *S. aureus* maintains millimolar levels of reduced CoA as its predominant thiol and, like most of the Gram-positive bacteria, essentially no GSH. Newton et al. (1996), supra; Newton et al. (1989), supra. CoA is required throughout metabolism as a cofactor in acyl transfer reactions and likely has additional functions in *S. aureus* analogous to those of GSH in other organisms.

Other organisms that utilize alternative thiols produce an enzyme analogous to GSR. The preferred substrate for such an enzyme is the disulfide of the predominant thiol in the cell. Shames et al. (1986) *Biochemistry* 25:3519–3526; Swerdlow et al. (1983) *J. Bacteriol.* 153:475–484. All such enzymes belong to a widespread family of pyridine nucleotide dependent disulfide reductases that include GSR, lipoamide dehydrogenase, and mercuric reductase. Most of these enzymes are homodimeric flavoproteins of $M_r\sim100$ kD that utilize a conserved active-site disulfide bond to effect catalysis.

Antimicrobial agents commonly used to combat microorganism infections generally interfere with a critical step in the metabolism of the microorganism resulting in growth inhibition or death thereof. However, pathogenic microorganisms, including staphylococci and enterococci, are developing resistance, and in many cases multiple resistances, to existing antimicrobial agents.

*S. aureus* is an opportunistic pathogen of increasing medical concern. It can be aggressively invasive, spreading rapidly through soft tissues, directly invading bones and even entering the bloodstream in which it may produce septic shock and disseminated intravascular coagulation. Two categories of disease may be ascribed to staphylococci: those related to toxins produced by the organism (*S. aureus* exclusively), including gastroenteritis, toxic shock syndrome, scalded skin syndrome, and the like; and those related to direct invasion and systemic spread of the organism, including dermal infections, bone and joint infections, staphylococcal pneumonia and empyema, meningitis, cerebritis, endocarditis, bacteremia, septic shock, and the like.

Strains of β-lactam antibiotic resistant staphylococci (BLARS), otherwise referred to as methicillin-resistant *S. aureus* (MRSA), have become a widespread cause of fatal nosocomial infection. Infections caused by such resistant staphylococci are treated predominantly by the "last resort" antibiotic, vancomycin. Newer antimicrobial agents that may be effective against staphylococcal infections include the investigational agent teichoplanin and the quinolones; however, recent data indicate increasing quinolone resistance. Since vancomycin resistance would essentially exhaust the current antibiotic therapeutic arsenal, it is now mandatory to identify new cellular targets and new chemotherapeutic agents effective against MRSA.

Accordingly, there is a need for new antimicrobial agents to which microorganisms are susceptible. The ability to discover and use such agents would be augmented by the availability of new cellular targets. Acquired resistance that protects against or compensates for disruption of one metabolic pathway by a particular class of antimicrobial agents would be unlikely to have a similarly protective or compensatory effect for disruption of a distinct metabolic pathway.

SUMMARY OF THE INVENTION

The inventors herein have identified a family of enzymes that catalyze the specific NADPH- or NADH-dependent reduction of CoA disulfide. The enzyme, Coenzyme A disulfide reductase (CoADR), catalyzes the specific reduction of Coenzyme A disulfide to Coenzyme A with the concomitant oxidation of NADPH to NADP$^+$ (or NADH to NAD$^+$) as shown below:

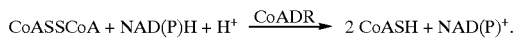

This is a significant metabolic function in staphylococci, enterococci, other Gram-positive bacteria, and other microorganisms that do not produce glutathione (GSH) but instead rely on Coenzyme A as the predominant cellular redox buffer. Inhibition of CoADR causes CoA disulfide to build up and depletes the pool of CoA that is available to act as a cofactor in numerous metabolic processes, including acyl transfer reactions, fatty acid biosynthesis, radical scavenging, peroxidase reactions, S-transferase drug resistance, other disulfide reductase reactions, disulfide isomerase reactions, and ribonucleotide reductase reactions. Such compromised cells are thus more likely to succumb to environmental challenges, such as those posed by a host immune system. As a result, inhibitors of CoADR activity are effective antimicrobial agents against S. aureus and other microorganisms that depend on CoA as a redox buffer. In addition, GSR need not be affected by specific inhibitors of CoADR. Thus, inhibition of microorganisms may be effected by inhibiting CoADR with few or no side effects in a eukaryotic host organism.

Accordingly, in one embodiment, the invention is directed to an isolated polypeptide comprising SEQ ID NO:18, SEQ ID NO:19 and SEQ ID NO:20 and having at least 34% overall identity to SEQ ID NO:1 wherein the polypeptide is a Coenzyme A disulfide reductase (CoADR). Preferably, the CoADR is from a Gram-positive coccus. More preferably, the CoADR is from a staphylococcus or enterococcus. Even more preferably, the CoADR is from *S. aureus, S. epidermidis, E. faecalis*, or *E. faecium*. Most preferably, the CoADR has the sequence of SEQ ID NO:1, SEQ ID NO:11, SEQ ID NO:13, SEQ ID NO:15 or SEQ ID NO:17.

In another embodiment, the invention is directed to a DNA sequence that encodes an CoADR polypeptide. Preferably, the DNA sequence encodes a CoADR from a Gram-positive coccus, more preferably, from a staphylococcus or enterococcus and even more preferably, from *S. aureus, S. epidermidis, E. faecalis*, or *E. faecium*. A most preferred DNA sequence has the sequence of SEQ ID NO:2, SEQ ID NO:10, SEQ ID NO:12, SEQ ID NO:14 or SEQ ID NO:16.

In yet another embodiment, the invention is directed to a recombinant vector comprising any of the aforementioned DNA sequences.

In still other embodiments, the invention is directed to messenger RNA encoded by the aforementioned DNA sequences, recombinant host cells transformed with vectors comprising the DNA and methods of producing recombinant polypeptides using the transformed cells.

In still another embodiment of the invention, monoclonal and polyclonal antibodies to the above-mentioned CoADR polypeptides are provided.

In still a further embodiment, the invention provides a probe for detecting the presence of a polynucleotide encoding a CoADR, comprising an olgonucleotide of at least eight nucleotides capable of specifically hybridizing to the polynucleotide under appropriate stringency conditions. Preferably, the probe detects the presence of a polynucleotide encoding a CoADR from a Gram positive coccus and more preferably, from *S. aureus, S. epidermidis, E. faecalis*, or *E. faecium*.

In a further embodiment, the invention is directed to a method of identifying compounds that modulate CoADR activity. Preferably, the compound modulates the CoADR activity from a Gram positive coccus and more preferably, from *S. aureus, S. epidermidis, E. faecalis*, or *E. faecium*.

In yet a further embodiment, the invention is directed to a method of treating an individual infected with a Gram-positive bacteria by administering a therapeutically effective amount of a CoADR activity-modulating compound. Preferably, the method of treatment is for a *Staphylococcus aureus* infection. In another preferred embodiment, the compound of the method is a pantethine derivative.

In yet another embodiment, the invention provides a class of antimicrobial agents that inhibit Coenzyme A disulfide reductase activity of a microorgansim, preferably, of a Gram-positive microorganism, and more preferably, from a Staphylococcus spp. or Enterococcus spp. A method of treating an individual suspected of having an infection due to a microorganism, comprising administering to the individual, an above-mentioned antimicrobial agent in a pharmaceutically acceptable excipient, in an amount effective for inhibiting or killing the microorganism is also provided.

In another embodiment, the invention provides a method of detecting a Gram-positive coccus in a sample containing or suspected to contain the Gram-positive coccus, comprising the steps of (a) contacting the sample with an oligonucleotide probe described above, thereby forming a complex; (b) detecting the presence of a hybrid complex; and correlating the presence of the hybrid complex with the presence of the Gram-positive coccus in the test sample. In a modification of the method, the sample may be contacted with an antibody (as described above) rather than an oligonucleotide probe, thereby forming an antibody-CoADR complex, detecting that complex and correlating the presence of the antibody-CoADR complex with the presence of the Gram-positive coccus in the test sample. In yet a further modification, a test sample is incubated with a composition comprising a substrate which, when catalytically activated by a Coenzyme A disulfide reductase from the Gram-positive coccus, produces a detectable signal. The signal is detected and the presence of the signal correlated with the presence of the Gram-positive coccus in the test sample.

In yet another embodiment, the invention provides a method for isolating a Coenzyme A reductase polypeptide from a bacterial cell medium.

In yet a further embodiment, the invention is directed to diagnostic kits comprising (a) an oligomer probe for detecting the presence of polynucleotides that encode CoADR, (b) an antibody capable of specifically binding to the CoADR polypeptide for detecting the presence and/or amount of a CoADR producing organism in a test sample, as well as for detecting of the presence of the organism, and (c) a CoADR polypeptide for screening compounds for CoADR-modulating activity or for screening test samples for the presence of a CoADR-antibody.

In still a further embodiment, the invention is directed to a method for inhibiting the growth of microorganisms that utilize Coenzyme A as their predominant redox buffer.

In still another embodiment, the invention provides a method for identifying a gene encoding a CoADR comprising the steps of: (a) isolating genomic DNA from an organism of interest; (b) amplifying by PCR at least one segment of the genomic DNA with SEQ ID NO:39 and SEQ ID NO:40 to generate a polynucleotide product; (c) sequencing the polynucleotide product and selecting as a probe, the sequenced product having at least 30% identity at the protein level to SEQ ID NO:1; (d) hybridizing the probe to digested fragments of the genomic DNA to detect a fragment comprising the gene; (e) sequencing the fragment; and (f) comparing the deduced amino acid sequence of the sequenced fragment to SEQ ID NO:1.

In yet another embodiment, the invention provides a method for identifying a gene encoding a CoADR comprising the steps of: (a) isolating genomic DNA from an organism of interest; (b) hybridizing a probe comprising a cdr gene or mixture of cdr genes to digested fragments of the genomic DNA to detect a fragment comprising the gene; (c) sequencing the fragment; and (d) comparing the deduced amino acid sequence of the sequenced fragment to SEQ ID NO:1.

These and other embodiments of the present invention will readily occur to those of ordinary skill in the art in view of the disclosure herein.

BRIEF DESCRIPTION OF THE FIGURES

FIG. 1 shows the nucleotide sequence (SEQ ID NO:1) of the S. aureus open reading frame encoding a CoADR.

FIG. 2 shows the deduced amino acid sequence (Cdr_Sa, SEQ ID NO:2) of the S. aureus CoADR derived from the nucleotide sequence of the open reading frame.

FIG. 3 shows the nucleotide sequence (top strand, SEQ ID NO:10) of the S. epidermidis open reading frame encoding a CoADR. The amino acid sequence (Cdr_Se, SEQ ID NO:11) deduced therefrom is shown beneath.

FIG. 4 shows the nucleotide sequence (top strand, SEQ ID NO:12) of the E. faecalis open reading frame encoding a CoADR The amino acid sequence (Cdr_Efa, SEQ ID NO:13) deduced therefrom is shown beneath.

FIG. 5 shows the nucleotide sequence (top strand, SEQ ID NO:14) of the E. faecium open reading frame encoding one CoADR. The amino acid sequence (CdrA_Efm, SEQ ID NO:15) deduced therefrom is shown beneath.

FIG. 6 shows the nucleotide sequence (top strand, SEQ ID NO:16) of the E. faecium open reading frame encoding a second CoADR. The amino acid sequence (CdrB_Efm, SEQ ID NO:17) deduced therefrom is shown beneath.

FIG. 7 shows the comparative alignment of Cdr_Sa, Cdr_Se, Cdr_Efa, CdrA_Efm, CdrB_Efm, (SEQ ID NO:1, SEQ ID NO:11, SEQ ID NO:13, SEQ ID NO:15, SEQ ID NO:17, respectively) and a consensus sequence generated therefrom. The consensus sequence was created in two parts. In the first part, representing amino acids 1–447, the identical amino acid from a plurality of at least four sequences was assigned to the corresponding consensus position; these amino acids are shown in capital letters in the consensus sequence. In the second part, where only three sequences could be compared (i.e. from amino acid 448 to amino acid 558), the identical amino acid from at least two sequences was assigned to the corresponding consensus position. This portion of the consensus sequence is shown in lower case letters.

DETAILED DESCRIPTION

The practice of the present invention will employ, unless otherwise indicated, conventional techniques of molecular biology, microbiology and recombinant DNA technology, which are within the skill of the art. Such techniques are explained fully in the literature. See, e.g., Sambrook, Fritsch & Maniatis, *Molecular Cloning: A Laboratory Manual*, Second Edition (1989); *DNA Cloning*, Vols. I and II (D. N. Glover ed. 1985); Perbal, B., *A Practical Guide to Molecular Cloning* (1984); the series, *Methods In Enzymology* (S. Colowick and N. Kaplan eds., Academic Press, Inc.); *Transcription and Translation* (Hames et al. eds. 1984); *Gene Transfer Vectors For Mammalian Cells* (J. H. Miller et al. eds. (1987) Cold Spring Harbor Laboratory, Cold Spring Harbor, N.Y.); Scopes, *Protein Purification: Principles and Practice* (2nd ed., Springer-Verlag); and *PCR: A Practical Approach* (McPherson et al. eds. (1991) IRL Press).

All patents, patent applications and publications cited herein, whether supra or infra, are hereby incorporated by reference in their entirety. As used in this specification and the appended claims, the singular forms "a," "an" and "the" include plural references unless the content clearly dictates otherwise.

A. Definitions

In describing the present invention, the following terms will be employed, and are intended to be defined as indicated below.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, such as by methylation and/or by capping, and unmodified forms of the polynucleotide.

Figure 2:
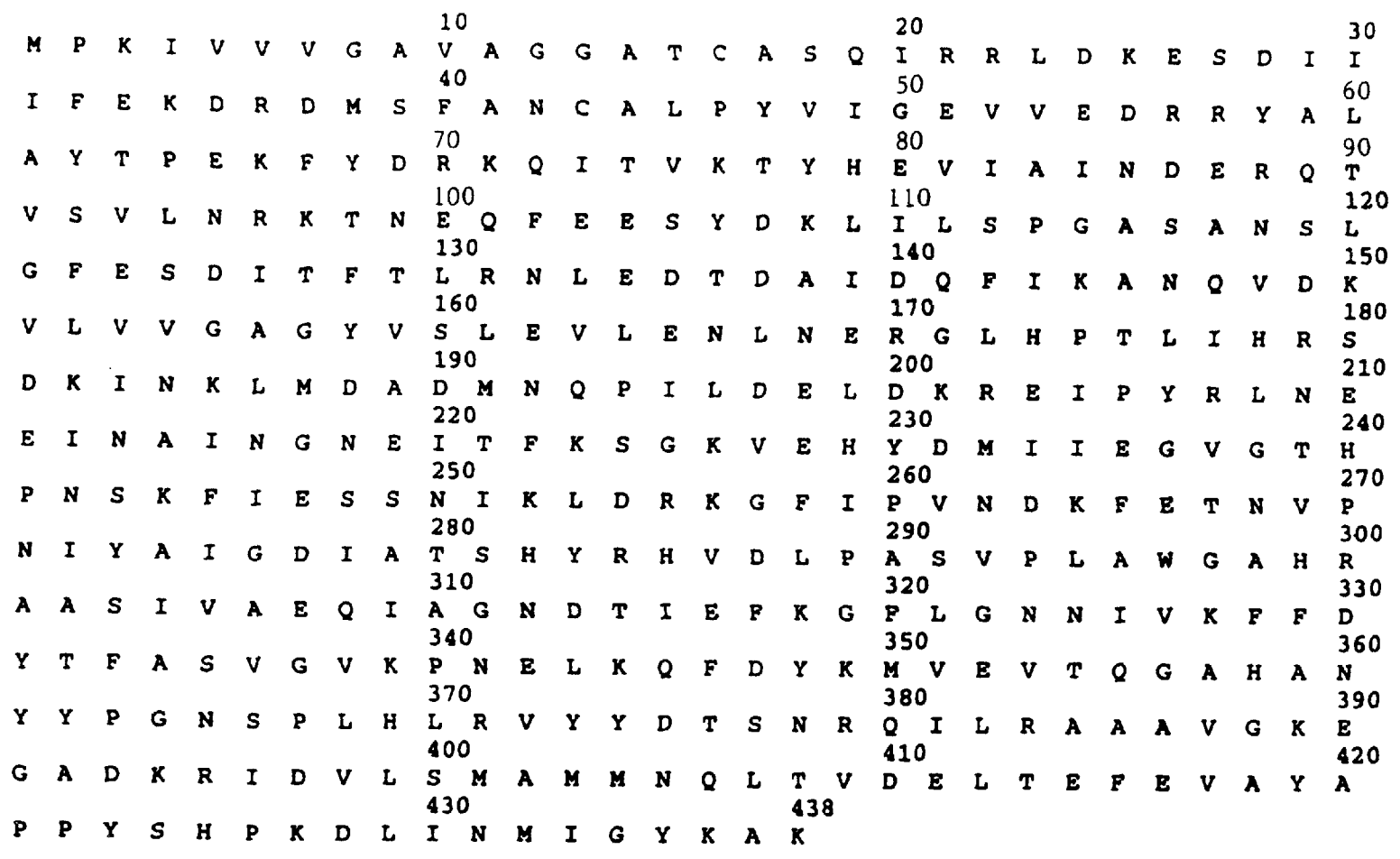

"Polypeptide" and "protein" are used interchangeably herein and indicate a molecular chain of amino acids linked through peptide bonds. The terms do not refer to a specific length of the product. Thus, peptides, oligopeptides, and proteins are included within the definition of polypeptide. The terms include post-translation modifications of the polypeptide, for example, glycosylations, acetylations, phosphorylations, and the like. In addition, protein fragments, analogs, muteins, fusion proteins and the like are included within the meaning of polypeptide. Thus, by "CoADR polypeptide" is meant a polypeptide, whether isolated, recombinant or synthetic, comprising an amino acid sequence identical to that depicted in FIG. 2, and fragments thereof that include only so much of the molecule as necessary for the polypeptide to retain biological activity, e.g., catalytic and/or immunological activity, as well as analogs, mutated or variant proteins, and the like, thereof that retain such activity.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vectors or other transfer DNA, immaterial of the method by which the DNA is introduced into the cell or the subsequent disposition of the cell. The terms include the progeny of the original cell which has been transfected.

A "vector" is a replicon in which another polynucleotide segment is attached, such as to bring about the replication and/or expression of the attached segment. The term includes expression vectors, cloning vectors, and the like.

The term "control sequence" refers to a polynucleotide sequence which effects the expression of coding sequences to which it is ligated. The nature of such a control sequence differs depending upon the host organism. In prokaryotes, such control sequences generally include a promoter, a ribosomal binding site, and a terminator. In eukaryotes, such control sequences generally include a promoter, a terminator and, in some instances, an enhancer. The term "control sequence" thus is intended to include at a minimum all components necessary for expression, and also may include additional components whose presence is advantageous, for example, leader sequences.

A "coding sequence" is a polynucleotide sequence that is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences. Mutants or analogs may be prepared by the deletion of a portion of the coding sequence, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences. A coding sequence may be operably linked to control sequences that direct the transcription of the polynucleotide whereby said polynucleotide is expressed in a host cell The term "transfection" refers to the insertion of an exogenous polynucleotide into a host cell, irrespective of the method used for the insertion, or the molecular form of the polynucleotide that is inserted. For example, injection, direct uptake, transduction, and f-mating are included. Furthermore, the insertion of a polynucleotide per se and the insertion of a plasmid or vector comprised of the exogenous polynucleotide are also included. The exogenous polynucleotide may be directly transcribed and translated by the cell, maintained as a nonintegrated vector, for example, a plasmid, or alternatively, may be stably integrated into the host genome.

By the term "degenerate variant" or "structurally conserved mutation" is intended a polynucleotide containing changes in the nucleic acid sequence thereof, such as insertions, deletions or substitutions, that encodes a polypeptide having the same amino acid sequence as the polypeptide encoded by the polynucleotide from which the degenerate variant is derived.

The term "isolated," when referring to a polynucleotide or a polypeptide, intends that the indicated molecule is present in the substantial absence of other similar biological macromolecules of the same type. The term "isolated" as used herein means that at least 75 wt. %, more preferably at least 85 wt. %, more preferably still at least 95 wt. %, and most preferably at least 98 wt. % of a composition is the isolated polynucleotide or polypeptide. An "isolated polynucleotide" that encodes a particular polypeptide refers to a polynucleotide that is substantially free of other nucleic acid molecules that do not encode the subject polypeptide; however, the molecule may include conservative mutations as defined herein.

The term "test sample" refers to a component of an individual's body which is the source of an analyte, such as antibodies or antigens of interest. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitorurinary tracts, tears, saliva, milk, white blood cells, myelomas and the like; biological fluids such as cell culture supernatants; fixed tissue specimens; and fixed cell specimens.

The following single-letter amino acid abbreviations are used throughout the text:

| Alanine | A | Arginine | R |
|---|---|---|---|
| Asparagine | N | Aspartic acid | D |
| Cysteine | C | Glutamine | Q |
| Glutamic acid | E | Glycine | G |
| Histidine | H | Isoleucine | I |
| Leucine | L | Lysine | K |
| Methionine | M | Phenylalanine | F |
| Proline | P | Serine | S |
| Threonine | T | Tryptophan | W |
| Tyrosine | Y | Valine | V |

B. General Methods

The present invention is based on the identification of CoADRs, as well as a polynucleotides encoding the CoADRs, and methods of making the CoADRs. The invention includes not only the enzymes but also methods for screening compounds for pharmacological activity using the enzymes, cells expressing the enzymes, monoclonal antibodies to the enzymes and the use of the antibodies to diagnose microbial infections/disease. Methods for identifying CoADRs are also provided.

The present invention provides polypeptides (CoA disulfide reductases) which catalyze the reduction of CoA disulfide in the presence of a reduced pyridine nucleotide. A most preferred pyridine nucleotide is NADPH. A CoADR of the invention comprises (a) a sequence having at least 34% identity to SEQ ID NO:1;

(b) a peptide sequence Gly-(Ala/Gly)-Val-Ala-Gly-Gly (SEQ ID NO:18);

(c) a peptide sequence Gly-Xaa$_1$-Gly-Xaa$_2$-Xaa$_3$-(Ser/Gly) (SEQ ID NO:19)) wherein Xaa$_1$, Xaa$_2$, and Xaa$_3$ are any L-amino acids;

(d) a peptide sequence Ser-(Phe/Tyr)-Xaa$_1$-Xaa$_2$-Cys (SEQ ID NO:20) wherein Xaa$_1$ and Xaa$_2$ are as defined above. Preferably, Xaa$_1$ in both SEQ ID NO:19 and SEQ ID NO:20 is Ala. SEQ ID NO:18 represents a sequence motif which has been shown to bind to the adenosine diphophate (ADP) moiety of flavin adenine dinucleotide (FAD), see Bellamcina, C. R., FASEB Journal, 10: 1257–1269 (1996). In the specific embodiments exemplified in FIG. 7, SEQ ID NO:18 is shown at amino acid positions 8–13 of SEQ ID NOs:1, 11, 13, 15, and 17. SEQ ID NO:19 also represents an ADP binding motif but binds to the ADP moiety of the pyridine nucleotide NADH or NADPH (Bellamcina, C. R., 1996, op. cit.). In FIG. 7, SEQ ID NO:19 is found at amino acid positions 159–164 of SEQ ID NOs:1, 11, 13, 15, and 17. SEQ ID NO:20 represents a motif for the catalytic active site of a CoADR of the invention. It has been shown, that the active site of other disulfide reductases have at least one Cys residue (Claiborne, A. et al., Trends in Biochemical Sciences 17: 183–186 (1992). In the embodiments of FIG. 7, SEQ ID NO:20 is shown at amino acid positions 39–43 of SEQ ID NOs: 1, 11, 13, 15, and 17.

A CoADR of the present invention may be obtained from any organism in which it is found by means well known to those of ordinary skill in the art. Preferred CoADRs are CoADRs from gram positive cocci. Of those which are preferred, even more preferred CoADRs are from staphylococci and enterococci. Most preferred CoADRs are from *S. aureus, S. epidermidis, Enterococcus faecalis* and *Enterococcus faecium*. Furthermore, a CoADR of the present is at least 34% identical overall (at the amino acid level) to SEQ ID NO:1, but more preferably, at least 37% identical, and even more preferably, at least 50% identical to SEQ ID NO:1.

The enzyme can be isolated directly from bacteria as follows. Bacteria can be cultured in a suitable culture medium, such as trypticase soy broth (TSB). The bacteria are then removed from the culture medium using standard techniques known in the art, such as by centrifugation or microfiltration or a combination of the two. For example, microfiltration using an appropriate filter will suffice to remove unwanted cellular debris.

Bacteria thus obtained are prepared to release the contents of the cytoplasm. Bacterial cells may be broken using methods and/or reagents known in the art that do not adversely affect the structure and/or the activity of the CoADR, e.g., exposure to freeze-thaw cycles, exposure to an ultrasonic disintegrator, homogenization, bead milling, chemical or enzymatic cell lysis, and the like. In one preferred method, cells are incubated in a buffer containing lysostaphin, a lytic agent for S. aureus, and then passed through a French pressure cell. In a second preferred method, particularly preferred for entercocci, the cells are incubated in a mixture of lytic agents including lysozyme, mutanolyase, and N-acetylglucosamidase.

The bacterial cell medium thus prepared can be further processed to separate the protein from the cellular debris, and provide an initial stage of purification and volume reduction. For example, the lysate obtained from the previous step may be processed by a primary separation procedure such as ultrafiltration, that is passage through a filter having a particular weight cut-off, to concentrate the sample by reducing the water and salts content. Alternatively, the lysate may be precipitated by neutral salts such as ammonium sulphate, organic solvents such as ethanol, or other agents for recovering and purifying the protein. Preferably, in the case of S. aureus, CoADR is precipitated from the lysate by adding ammonium sulfate to the lysate to approximately 40%, preferably 50%, saturation. The supernatant of the same is collected by, e.g., centrifugation, and the ammonium sulfate is adjusted to 90%, preferably 80%, saturation. The treated precipitate thus obtained is collected and used in further purification steps.

A number of protein purification operations may be used to further purify a CoADR including adsorption chromatography, ion-exchange chromatography, hydrophobic interaction chromatography, affinity chromatography, chromatofocussing, gel filtration, reversed-phase liquid chromatography, phosphocellulose chromatography, hydroxyapatite chromatography or lectin chromatography, any combination of such techniques. Protein refolding steps can be used, as necessary, in completing configuration of the protein. Finally, high performance liquid chromatography (HPLC) can be employed for final purification steps.

Preferably, a first purification step will be one of high resolution in order to minimize the number of stages used and hence maximize yield. More preferably, the first purification step is an affinity purification using, e.g., 2',5'-ADP linked to an appropriate support matrix as the affinity adsorbent. The affinity purification may be done in a batch mode, by which the sample is adsorbed onto the affinity matrix and eluted in a single step, by progressive elution without a change in the elution buffer or by a gradient elution, in which the buffer is continuously changed to effect elution of the enzyme. Preferably, the CoADR is eluted from the affinity matrix with a linear salt gradient.

A subsequent purification step may also be used to "polish" the preparation obtained from the affinity purification step. Preferably, the subsequent step is an ion-exchange purification step, more preferably an anion-exchange purification step. Suitable anion exchangers include a wide variety of materials, known in the art. Particularly preferred are strong anion exchangers capable of binding CoADR over a wide pH range. For example, quaternary ammonium and quaternary alkylalkanolammonium anion exchange matrices are particularly useful for use herein. Useful matrix materials include but are not limited to, cellulose matrices, such as fibrous, microgranular and beaded matrices; agarose, dextran, polyacrylate, polyvinyl, polystyrene, silica and polyether matrices; and composites. Particularly preferred herein are matrices containing the functional ligand R—$NH_4^+$, preferably sulfopropyl resins. Representative matrices include MonoQ HR 5/5 or SigmaChrom IEX-Q.

Once purified, the amino acid sequences of the proteins can be determined, e.g., by repetitive cycles of Edman degradation, followed by amino acid analysis by HPLC. Other methods of amino acid sequencing are also known in the art. Using such techniques, the N-terminal fourteen amino acids of, for example, purified S. aureus CoADR polypeptide has been determined to be Pro-Lys-Ile-Val-Val-Val-Gly-Ala-Val-Ala-Gly-Gly-Ala-Thr (SEQ ID NO:3). The complete deduced amino acid sequence is shown in FIG. 2.

Based on knowledge of the amino acid sequence, DNA encoding the enzyme can be derived from genomic or cDNA, prepared by synthesis, or by a combination of techniques. The DNA can then be used to express the CoADR or as a template for the preparation of RNA using methods well known in the art (see, Sambrook et al., supra).

More particularly, DNA encoding the CoADR may be obtained from an appropriate DNA library, e.g., an S. aureus genomic DNA library. DNA libraries may be probed using the procedure described by Grunstein et al. (1975) *Proc. Natl. Acad. Sci. USA* 73:3961. Briefly, the DNA to be probed is immobilized on nitrocellulose filters, denatured and prehybridized with a buffer which contains 0–50% formamide, 0.75 M NaCl, 75 mM Na citrate, 0.02% (w/v) each of bovine serum albumin (BSA), polyvinyl pyrollidone and Ficoll®, 50 mM Na phosphate (pH 6.5), 0.1% sodium dodecyl sulfate (SDS) and 100 μg/ml carrier denatured DNA. The percentage of formamide in the buffer, as well as the time and temperature conditions of the prehybridization and subsequent hybridization steps, depends on the stringency required. Oligomeric probes which require lower stringency conditions are generally used with low percentages of formamide, lower temperatures, and longer hybridization times. Probes containing more than 30 or 40 nucleotides such as those derived from cDNA or genomic sequences generally employ higher temperatures, for example, about 40° C. to 42° C., and a high percentage, for example, 50% formamide. Following prehybridization, a $^{32}$P-labelled oligonucleotide probe is added to the buffer, and the filters are incubated in this mixture under hybridization conditions. After washing, the treated filters are subjected to autoradiography to show the location of the hybridized probe DNA in corresponding locations on the original agar plates is used as the source of the desired DNA.

Synthetic oligonucleotides may be prepared using an automated oligonucleotide synthesizer such as that described by Warner (1984) *DNA* 3:401. If desired, the synthetic strands may be labelled with $^{32}$P by treatment with polynucleotide kinase in the presence of $^{32}$P-ATP, using standard conditions for the reaction. DNA sequences including those isolated from genomic or cDNA libraries, may be modified by known methods which include site-directed mutagenesis as described by Zoller (1982) *Nucleic Acids Res.* 10:6487. Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. Culture of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labelled synthetic probe at temperatures and conditions suitable for hybridization with the correct strand, but not with the unmodified sequence. The sequences which have been identified by hybridization are recovered and cloned.

Once produced, the DNA may then be incorporated into a cloning vector or an expression vector for replication in a suitable host cell. Vector construction employs methods known in the art. Generally, site-specific DNA cleavage is performed by treating with suitable restriction enzymes under conditions which generally are specified by the manufacturer of these commercially available enzymes. Usually, about 1 microgram ($\mu$g) of plasmid or DNA sequence is cleaved by 1–10 units of enzyme in about 20 $\mu$l of buffer solution by incubation at 37° C. for 1 to 2 hours. After incubation with the restriction enzyme, protein is removed by phenol/chloroform extraction and the DNA recovered by precipitation with ethanol. The cleaved fragments may be separated using polyacrylamide or agarose gel electrophoresis methods, according to methods known by those of skill in the art.

Sticky end cleavage fragments may be blunt ended using *E. coli* DNA polymerase 1 (Klenow) in the presence of the appropriate deoxynucleotide triphosphates (dNTPs) present in the mixture. Treatment with S1 nuclease also may be used, resulting in the hydrolysis of any single stranded DNA portions.

Ligations are performed using standard buffer and temperature conditions using T4 DNA ligase and ATP. Sticky-end ligations require less ATP and less ligase than blunt-end ligations. When vector fragments are used as part of a ligation mixture, the vector fragment often is treated with bacterial alkaline phosphatase (BAP) or calf intestinal alkaline phosphatase to remove the 5'-phosphate and thus prevent religation of the vector. Alternatively, restriction enzyme digestion of unwanted fragments can be used to prevent ligation.

For standard vector constructions, ligation mixtures are transformed into a suitable host, and successful transformants selected by antibiotic resistance or other markers. Plasmids from the transformants can then be prepared according to the method of Clewell et al. (1969) *Proc. Natl. Acad. Sci. USA* 62:1159 usually following chloramphenicol amplification as reported by Clewell et al. (1972) *J. Bacteriol.* 110:667. The DNA is isolated and analyzed usually by restriction enzyme analysis and/or sequencing. Sequencing may be by the well-known dideoxy method of Sanger et al. (1977) *Proc. Natl. Acad. Sci. USA* 74:5463) as further described by Messing et al. (1981) *Nucleic Acid Res.* 9:309, or by the method reported by Maxam et al. (1980) *Meth. Enzymol.* 65:499. Problems with band compression, which are sometimes observed in GC rich regions, are overcome by use of T-deazoguanosine according to the method reported by Barr et al. (1986) *Biotechniques* 4:428.

Host cells are genetically engineered (transduced or transformed or transfected) with the vectors of this invention which may be a cloning vector or an expression vector. The vector may be in the form of a plasmid, a viral particle, a phage, etc. The engineered host cells can be cultured in conventional nutrient media modified as appropriate for activating promoters, selecting transformants or amplifying the CoADR-encoding polynucleotide. The culture conditions, such as temperature, pH and the like, are those previously used with the host cell selected for expression, and will be apparent to those of skill in the art.

Both prokaryotic and eukaryotic host cells may be used for expression of desired coding sequences when appropriate control sequences that are compatible with the designated host are used. Among prokaryotic hosts, *Escherichia coli* is frequently used. Expression control sequences for prokaryotes include promoters, optionally containing operator portions, and ribosome binding sites. Transfer vectors compatible with prokaryotic hosts are commonly derived from the plasmid pBR322 that contains operons conferring ampicillin and tetracycline resistance, and the various pUC vectors, that also contain sequences conferring antibiotic resistance markers. These markers may be used to obtain successful transformants by selection. Commonly used prokaryotic control sequences include the beta-lactamase (penicillinase), lactose promoter system (Chang et al. (1977) *Nature* 198:1056), the tryptophan promoter system (reported by Goeddel et al. (1980) *Nucleic Acid Res.* 8:4057) and the lambda-derived P1 promoter and N gene ribosome binding site (Shimatake et al. (1981) *Nature* 292:128) and the hybrid Tac promoter (De Boer et al. (1983) *Proc. Natl. Acad. Sci. USA* 292:128) derived from sequences of the trp and lac UV5 promoters. The foregoing systems are particularly compatible with *E. coli*; however, other prokaryotic hosts such as strains of Bacillus or Pseudomonas may be used if desired, with corresponding control sequences.

Eukaryotic hosts include yeast and mammalian cells in culture systems. *Saccharomyces cerevisiae* and *S. carlsbergensis* are commonly used yeast hosts, and are convenient fungal hosts. Yeast-compatible vectors carry markers that permit selection of successful transformants by conferring protrophy to auxotrophic mutants or resistance to heavy metals on wild-type strains. Yeast compatible vectors may employ the 2-micron origin of replication (Broach et al. (1983) *Meth. Enzymol.* 101:307), the combination of CEN3 and ARS1 or other means for assuring replication, such as sequences that will result in incorporation of an appropriate fragment into the host cell genome. Control sequences for yeast vectors are known in the art and include promoters for the synthesis of glycolytic enzymes, including the promoter for 3-phosphoglycerate kinase. See, for example, Hess et al. (1968) *J. Adv. Enzyme Reg.* 7:149, Holland et al. (1978) *Biochemistry* 17:4900, and Hitzeman (1980) *J. Biol. Chem.* 255:2073. Terminators also may be included, such as those derived from the enolase gene as reported by Holland (1981) *J. Biol. Chem.* 256:1385. It is contemplated that particularly useful control systems are those that comprise the glyceraldehyde-3-phosphate dehydrogenase (GAPDH) promoter or alcohol dehydrogenase (ADH) regulatable promoter, terminators also derived from GAPDH, and, if secretion is desired, leader sequences from yeast alpha factor. In addition, the transcriptional regulatory region and the transcriptional initiation region which are operably linked may be such that they are not naturally associated in the wild-type organism.

Mammalian cell lines available as hosts for expression are known in the art and include many immortalized cell lines which are available from the American Type Culture Collection. These include HeLa cells, Chinese hamster ovary (CHO) cells, baby hamster kidney (BHK) cells, and others. Suitable promoters for mammalian cells also are known in the art and include viral promoters such as that from Simian Virus 40 (SV40), Rous sarcoma virus (RSV), adenovirus (ADV), bovine papilloma virus (BPV), cytomegalovirus (CMV). Mammalian cells also may require terminator sequences and poly A addition sequences; enhancer sequences which increase expression also may be included, and sequences which cause amplification of the gene also may be desirable. These sequences are known in the art. Vectors suitable for replication in mammalian cells may include viral replicons, or sequences which insure integration of the appropriate sequences encoding the *S. aureus* CoADR into the host genome.

Other eukaryotic systems are also known, as are methods for introducing polynucleotides into such systems, such as into amphibian cells, using known methods, and insect cells using methods described in Summers and Smith (1987), *Texas Agricultural Experiment Station Bulletin No.* 1555 (1987), and the like.

Transformation may be by any known method for introducing polynucleotides into a host cell, including packaging the polynucleotide in a virus and transducing a host cell with the virus, by direct uptake of the polynucleotide by the host cell, and the like. The transformation procedures selected depend upon the host to be transformed. Bacterial transformation by direct uptake generally employs treatment with calcium or rubidium chloride. Cohen (1972) *Proc. Natl. Acad. Sci. USA* 69:2110. Yeast transformation by direct uptake may be conducted using the calcium phosphate precipitation method of Graham et al. (1978) *Virology* 52:526, or modification thereof.

Expression of active CoADR can be assayed calorimetrically by monitoring the NADPH- and CoA disulfide-dependent reduction of 5,5'-dithio-bis-2-nitrobenzoic acid (DTNB) at 412 nm. This reaction is suitable for screening compounds for their CoADR-inhibiting activity. Alternatively, expression of CoADR can be monitored using an ELISA assay and antibodies prepared to the isolated CoADR enzyme. The enzyme is recovered and purified from recombinant host cell cultures expressing the same by known methods as described above.

The CoADR polypeptide, or fragments thereof, of the present invention may also be synthesized by conventional techniques known in the art, for example, by chemical synthesis such as solid phase peptide synthesis. Such methods are known to those skilled in the art. In general, these methods employ either solid or solution phase synthesis methods, well known in the art. See, e.g., J. M. Stewart and J. D. Young, *Solid Phase Peptide Synthesis*, 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3–254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis.

Once obtained, the enzyme may be used to identify compounds that modulate CoADR activity. Thus, as described above, enzyme activity and the effects of compounds on enzyme activity can be assayed calorimetrically by monitoring the NADPH- and CoA disulfide-dependent reduction of 5,5'-dithio-bis-2-nitrobenzoic acid (DTNB) at 412 nm. Using this assay method, it has been determined that pantethine derivatives are effective as inhibitors of CoADR activity. For example, purification or expression of *S. aureus* CoADR and screening for compounds that inhibit the enzyme activity provides a method for rapid selection of compounds with enzyme-inhibiting activity.

Accordingly, compounds that inhibit CoADR are considered potential therapeutic agents for use in treating several disorders including, without limitation, staphylococcal, enterococcal and other Gram-positive bacterial infections, and the like, in which such agents may be useful in preventing growth and/or reproduction of the infecting microorganism when administered in a suitable pharmaceutical composition. Examples of such diseases for which CoADR inhibitors are useful therapeutic agents include, gastroenteritis, toxic shock syndrome, scalded skin syndrome, dermal infections, bone and joint infections, pneumonia and empyema, meningitis, cerebritis, endocarditis, bacteremia, septic shock, septicemia, food poisoning, enteritis, and the like.

The inhibitory compounds of the present invention can be formulated into therapeutic compositions in a variety of dosage forms such as, but not limited to, liquid solutions or suspensions, tablets, pills, powders, ointments suppositories, polymeric microcapsules or microvesicles, liposomes, and injectable or infusible solutions. The preferred form depends upon the mode of administration and the particular microorganism and disease type targeted. The compositions also preferably include pharmaceutically acceptable vehicles, carriers or adjuvants, well known in the art, such as human serum albumin, ion exchangers, alumina, lecithin, buffer substances such as phosphates, glycine, sorbic acid, potassium sorbate, and salts or electrolytes such as protamine sulfate. Suitable vehicles are, for example, water, saline, dextrose, glycerol, ethanol, or the like, and combinations thereof. Actual methods of preparing such compositions are known, or will be apparent, to those skilled in the art. See, e.g., *Remington's Pharmaceutical Sciences*, Mack Publishing Company, Easton, Pa., 18th edition, 1990.

The above compositions can be administered using conventional modes of delivery including, but not limited to, intravenous, intraperitoneal, oral, intralymphatic, or subcutaneous administration. Local administration to a tissue in question, or to a site of infection, e.g., direct injection into an infected joint, will also find use with the present invention.

Therapeutically effective doses will be easily determined by one of skill in the art and will depend on the severity and course of the disease, the patient's health and response to treatment, and the judgment of the treating physician.

Furthermore, the CoADR polypeptide can be used to prepare polyclonal or monoclonal antibodies using techniques that are well known in the art. The CoADR can be directly purified from a culture of an organism which produces it naturally or can be obtained using the recombinant technology outlined below, i.e., a recombinant cell that expresses the enzyme can be cultured to produce quantities of the enzyme that can be recovered and isolated. Alternatively, the enzyme can be synthesized using conventional polypeptide synthetic techniques as provided below. Monoclonal antibodies that display specificity and selectivity for the enzyme can be labeled with a detectable moiety, e.g., a fluorescent moiety, and used in in vitro, or in situ immunofluorescent assays, or the like. The antibodies can be used to identify an organism such as a pathogenic bacterium for immunodiagnostic purposes.

In addition, DNA encoding the CoADR, or RNA derived therefrom, can be used to design oligonucleotide probes for detecting a microbe present in a host organism. As used herein, the term "probe" refers to a structure comprised of a polynucleotide, as defined above, which contains a nucleic acid sequence complementary to a nucleic acid sequence present in a target polynucleotide. The polynucleotide regions of probes may be composed of DNA, and/or RNA, and/or synthetic nucleotide analogs such as morpholino compounds and peptide nucleic acid ("PNA") analogs. Such probes may be used in in vitro or in situ hybridization assays, or the like, and are useful, for example, for the diagnosis of microbial infections.

Using a determined portion of the isolated CoADR-encoding polynucleotide, oligomers of approximately eight or more nucleotides can be prepared, either by excision or synthetically, which hybridize with the CoADR-encoding polynucleotide. Such oligomers are useful, for example, for detecting the presence of bacteria in diseased individuals. The natural or derived probes for CoADR polynucleotides are a length that allows the detection of unique sequences by hybridization. While six to eight nucleotides may be a workable length, sequences of ten to twelve nucleotides are preferred, and those of about twenty nucleotides most preferred. These probes can be prepared using routine, standard methods including automated oligonucleotide synthetic methods.

When the oligonucleotide probes are to be used as diagnostic reagents, the test sample to be analyzed, such as blood or serum, may be treated such as to extract a nucleic acid fraction thereof. The resulting nucleic acid from the sample may be subjected to gel electrophoresis or other size separation techniques, or the nucleic acid sample may be dot-blotted without size separation. The sample is then exposed to an oligonucleotide probe that has been detectably labelled. Suitable labels and methods for attaching labels to probes are known in the art, and include but are not limited to radioactive labels incorporated by nick translation or kinasing, biotin, fluorescent and chemiluminescent probes, enzymes which catalyze the production of a detectable product such as horseradish peroxidase, alkaline phosphatase, β-galactosidase, and the like. The nucleic acids extracted from the sample are then treated with the labelled probe under conditions of suitable hybridization stringency.

The stringency of hybridization is determined by a number of factors during the washing procedure, including temperature, ionic strength, length of time and concentration of formamide. Sambrook et al., supra. Hybridization can be carried out by a number of various techniques. Amplification of the sample nucleic acid, if required, can be performed, for example, by ligase chain reaction (LCR), polymerase chain reaction (PCR), Q-beta replicase, NASBA, or other techniques well known in the art. The amplified nucleic acids then may be detected using a hybridization assay such as those known in the art.

CoADR, antibodies thereto, as well as polynucleotides encoding CoADR or portions thereof, can be provided in diagnostic kits. For example, oligomer probes capable of specifically hybridizing to a polynucleotide encoding a CoADR can be packaged in diagnostic kits which include the probe nucleic acid sequence which may be labelled. Alternatively, the probe may be provided unlabelled and the ingredients for labelling could be included with the kit. The kit also may contain other suitably packaged reagents and materials needed or desirable for the particular hybridization protocol, for example, standards as well as instructions for performing the assay.

In addition, kits can include reagents for detecting of the presence and/or amount of a CoADR in a test sample, as well as for detecting of the presence of an organism which produces the CoADR. Such reagents can comprise, e.g., an antibody capable of specifically binding to the CoADR polypeptide.

Furthermore, kits containing a CoADR polypeptide in a suitable container are provided for screening compounds for CoADR-modulating activity or for screening test samples for the presence of a CoADR-antibody. It is contemplated that reagents employed in the above kits can be provided in one or more containers such as vials or bottles, with each container containing a separate reagent such as a monoclonal antibody, or a cocktail of monoclonal antibodies, or a polypeptide (either recombinant or synthetic) employed in the assay. Other components such as buffers, controls, and the like, known to those of ordinary skill in art, may be included in such test kits. The kits will also include instructions for the use thereof.

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Experimental

STRAINS AND MEDIA.

Staphylococcus aureus R8325-4 (no prophage), used as a source of CoADR and genomic DNA, was obtained from John Iandolo, Kansas State University, Department of Pathobiology (Manhattan, Kans.). S. aureus was grown in tryptic soy broth (Difco Laboratories, Detroit, Mich.) at 30° C. under standard incubation conditions. Escherichia coli DH5α was from Gibco, BRL, strain BL21 (DE3) and plasmid pET22B(+) were from Novagen (Madison, Wis.). E. coli was grown in LB and TB medium at 37° C. When required, E. coli was grown in the presence of ampicillin (100–400 mg/mL).

MATERIALS.

Reduced nicotinamide adenine dinucleotide phosphate (NADPH), riboflavin, flavin adenine mononucleotide (FMN), flavin adenine dinucleotide (FAD), coenzyme A disulfide, glutathionyl-coenzyme A mixed disulfide, 3'-dephospho coenzyme A, 5,5'-dithio-bis(2-nitrobenzoic acid) (DTNB), lysostaphin, bicinchoninic acid solution, 4% copper sulphate pentahydrate solution, 2',5'-adenosine diphosphate (ADP)-Sepharose®; and phenylmethylsulphonyl fluoride (PMSF) were from Sigma (Mississauga, ON). 3'-dephospho CoA was oxidized to the disulfide by incubation at room temperature overnight in Tris-HCl (20 mM), pH 9.0, containing copper (5 μM). 4,4'-phosphopantetheine was formed by incubation of CoA with nucleotide pyrophosphatase. The thiol was oxidized as described above, and the disulfide was purified by high performance liquid chromatography (HPLC). All other chemicals were of reagent grade or better and were used without further purification.

GENERAL METHODS.

Isolation of S. aureus genomic DNA was carried out by standard methods, Novick (1991) Meth. Enzymol. 204:587–636. Oligonucleotides were prepared on a Beckman oligonucleotide synthesizer using standard phosphoramidite chemistry. Restriction enzymes and Taq DNA polymerase were from Gibco BRL, and T4 DNA ligase and calf intestine alkaline phosphatase were from New England Biolabs. DNA fragments and PCR products were routinely purified using Qiaquick spin columns (Qiagen, San Diego, Calif.). DNA fragments were labeled with digoxigenin by random primed PCR using the DIG DNA Labeling and Detection Kit (Boehringer Mannheim, Laval, Québec). Plasmids were purified on Qiawell cartridges (Qiagen) and sequenced using the Dye Termination Cycle Sequencing Kit and AmpliTaq DNA polymerase, FS (Perkin Elmer) and analyzed on an ABI 373 automated DNA sequence analyzer. CoADR was purified as described above. All other reagents were of standard grade and used without further purification.

Protein chromatography was performed on a Fast Phase Liquid Chromatography (FPLC) system (Pharmacia, Upsala) equipped with UV and conductivity flow cells. Sodium dodecylsulfate polyacrylamide gel electrophoresis (SDS-PAGE) and blotting of proteins were carried out using a Mini Protean Electrophoresis system (Bio-Rad, Richmond, Calif.) using a Tris-glycine buffer. Prestained protein standards for SDS-PAGE were from GibcoBRL and were 200, 97, 68, 43, 29, 18, and 14 kD. Molecular weight standards for gel filtration were from BioRad and were 670, 158, 44, 17, and 1.3 kD. Spectrophotometric measurements were performed on a thermal-stated Cary I spectrophotometer (Varian, Australia) using quartz cuvettes (500 ml) (Hellma, Concord, ON). Concentration of protein samples were carried out using centricon filters (Amicon). Dialysis tubing was from Spectrum Medical Industries, Inc.

Concentrations of FAD, NADPH and CoA disulfide (and dephosphoCoA disulfide) were measured spectrophotometrically at 340 nm ($e^{340}$=6220 $M^{-1}$ $cm^{-1}$), 260 nm ($e^{260}$=33,600 $M^{-1}$ $cm^{-1}$), and 450 nm ($e^{450}$=11,000 $M^{-1}$ $cm^{-1}$), respectively. DTNB assays were performed in Tris-HCl (20 mM), pH 8.0, containing EDTA (1 mM) (TE buffer), and were monitored at 412 nm for the nitrobenzothiolate anion ($e^{412}$=15,600 $M^{-1}$ $cm^{-1}$ (Ellman (1959) *Arch. Biochem. Biophys.* 82:70–77)). Protein concentrations were determined by reaction with bicinchoninic acid and copper sulfate (Deutscher (1990) in *Meth. Enzymol.*, vol. 182. San Diego: Academic Press, Inc.). During purification, CoADR activity in crude extracts was monitored by the NADPH and CoA disulfide dependent reduction of DTNB. DTNB and all substrates were added at 0.1 mM. For kinetic analysis of purified CoADR activity, the oxidation of NADPH was measured as the decrease in absorbance at 340 nm ($De^{340}$=6,220 $M^{-1}$ $cm^{-1}$), and was carried out in Tris-HCl (50 mM), pH 7.8, containing NaCl (50 mM).

GENE INACTIVATION.

Gene inactivation experiments described herein employ two types of plasmids. The plasmid used for cdr inactivation in *S. aureus* and *S. epidermidis* contains a temperature sensitive origin of replication for Staphylococcus such that, when the temperature is raised to 45° C., the plasmid cannot replicate. If the plasmid carries a segment of the host chromosome, recombination between the homologous segments will result in the integration of the plasmid. At 45° C., the integrated plasmid can be stably maintained employing selection for the genetic marker carried on the plasmid sequence. If the homologous chromosomal fragment represents a segment internal to a gene, recombination of the plasmid into the chromosome will cause disruption of the gene and result in the inactivation of the corresponding polypeptide. The cells carrying the inactivated gene are then propagated in appropriate growth medium to determine the extent of growth. If cells carrying the inactivated gene cannot be propagated or grow poorly, the disrupted gene is considered essential for growth or survival.

The plasmid used for gene disruption in *E. faecalis* and *E. faecium* is pACYC184, available from commercial suppliers such as New England Biolabs, Beverly, Mass. This plasmid does not replicate in enterococci (at any temperature). The same strategy is employed for inactivation of the cdr genes in enterococci as that decribed for staphylococci.

ANALYSIS OF THIOLS FROM *S. AUREUS*.

An analysis of the thiols produced by *S. aureus* was carried out by resuspending cell pellets (250 mg) in 50% acetonitrile in 20 mM Tris-HCl, pH 8.0, containing monobromobimane (mBB) (2 mM) and incubating the suspension at 60° C. for five minutes in the dark. Control samples are pretreated with N-ethylmaleimide (NEM) (2 mM) under the same conditions before the addition of mBB (to 2 mM). The cellular debris was removed by centrifugation, and the samples were diluted in 10 mM aqueous methane sulfonic acid for reverse phase HPLC analysis.

EXAMPLE 1

Identification of a Coenzyme A Disulfide Reductase from *S. aureus*

In order to identify the enzyme responsible for maintaining CoA in its reduced form, *S. aureus* extracts were analyzed for a disulfide reductase specific for CoA disulfide. An overnight culture (10 ml) of R8325-4 was centrifuged (5,000×g, 10 min), resuspended in 3 ml of TE buffer containing lysostaphin (5 mg/ml), and incubated at 37° C. for 30 min until the suspension became viscous. Glass beads (1 g) and PMSF (to 1 mM) were added, the mixture was vortexed for two minutes and then centrifuged (14,000×g, 10 min) to remove the insoluble cellular debris. The resulting viscous lysate was dialyzed exhaustively (3,600 $M_r$ cutoff) against TE buffer. The dialysate was then assayed for the pyridine nucleotide (1 mM) and CoA disulfide (1 mM) dependent reduction of DTNB (1 mM). The results of this analysis are shown in Table 1.

TABLE 1

Identification of an NADPH and coenzyme A dependent oxidoreductasen in extracts of *Staphylococcus aureus*. Shown is the ability of *S. aureus* extracts to reduce DTNB in the presence of various pyridine nucleotide and disulfide substrates.

| Pyridine nucleotide | Disulfide | | | | |
|---|---|---|---|---|---|
| | none | GSSG | cystine | pantethine | CoA disulfide |
| none | — | — | — | — | — |
| NADH | — | — | — | — | — |
| NADPH | +[a] | — | — | — | ++++ |

[a]A very low NADPH dependent reduction of DTNB was detected in some extracts, which was attributed to the thioredoxin/thioredoxin reductase system present in most organisms.

Table 1 shows the ability of dialyzed *S. aureus* extracts to reduce DTNB in the presence and absence of NADH, NADPH and various disulfide substrates. DTNB was reduced only when the extracts are incubated with both CoA disulfide and NADPH. NADH, GSSG, cystine and pantethine did not function in the NADPH-dependent reduction of DTNB. DTNB is reduced only when the extracts are incubated with both CoA disulfide and NADPH. NADH cannot be used in the CoA disulfide dependent reduction of DTNB, nor can GSSG, cystine, or pantethine function in the NADPH dependent reduction of DTNB. These results indicate that *S. aureus* produces a Coenzyme A disulfide reductase (CoADR) that catalyzes specifically the reduction of CoA disulfide by NADPH. A low level of NADPH-dependent and CoA disulfide-independent reduction of DTNB was detected and was attributed to thioredoxin/thioredoxin reductase.

EXAMPLE 2

Purification and Characterization of CoADR from *S. aureus*

A. PURIFICATION PROCEDURE.

CoADR was fractionated from cellular extracts of *S. aureus* by following the NADPH- and CoA disulfide-dependent reduction of DTNB. An overnight culture of *S. aureus* strain R8325-4 grown in TSB (10 ml) at 37° C. was used as an inoculum (0.4 ml) for each of ten 2 L flasks containing TSB (1 L). These cells were shaken (180 rpm) for 12 h at 37° C. before being harvested by centrifugation (7000×g, 15 min). All subsequent handling of the sample prior to chromatography was carried out at 4° C. The cell pellet was resuspended in a minimum of TE buffer containing PMSF (1 mM) and lysostaphin (0.5 mg), incubated at 37° C. with agitation for one hour (or until viscous), passed twice through a French pressure cell operating at 15,000 lb/in$^2$, and then centrifuged (15,000×g, 20 min) to remove insoluble cellular debris. The supernatant was brought to 50% saturation with $(NH_4)_2SO_4$, stirred for 15 min, and centrifuged (15,000×g, 10 min). The resulting supernatant was brought to 80% saturation with $(NH_4)_2SO_4$, centrifuged, and the pellet containing the CoADR activity was dissolved in a minimum of TE buffer containing PMSF (1 mM). The resulting solution was dialyzed exhaustively (3,500 $M_r$ cutoff) against TE buffer containing PMSF (1 mM).

All chromatography was carried out at room temperature. The dialyzed $(NH_4)_2SO_4$ fraction was applied (1.0 ml/min) to an 2',5'-ADP-Sepharose® affinity column (1 by 5 cm) equilibrated with buffer A, which was Tris-HCl (20 mM), pH 8.0. The column was washed with buffer A (25 ml) and then eluted with a linear gradient (35 ml) of NaCl (0–4 M) in buffer A. The fractions (1 ml) exhibiting CoADR activity were pooled, concentrated and diluted in buffer A twice to reduce conductivity, and applied (1.0 ml/min) to a MonoQ HR 5/5 anion exchange column (1 ml) equilibrated with buffer A. The column was washed with 5 ml of buffer A and eluted with a linear gradient (25 ml) of NaCi (0.3–0.6 mM) in buffer A. The purity of fractions showing CoADR activity was determined by SDS-PAGE (5% stacking gel; 12% separating gel) and silver staining.

A chart describing the purification of CoADR from 10 liters of *S. aureus* cells is shown in Table 2.

TABLE 2

Purification of Coenzyme A Disulfide Reductase from *Staphylococcus aureus*

| Fraction | Total units[a] | Protein (mg) | Specific activity (units/mg) | Purification (X fold) | Yield (%) |
|---|---|---|---|---|---|
| soluble extract | 3870 | 2560 | 1.51 | 1.0 | 100 |
| 50–80% amm. sulf. dialysate | 2200 | 246 | 8.7 | 5.8 | 57 |
| 2'–5' ADP-sepharose | 1800 | 0.84 | 2143 | 1420 | 47 |
| MonoQ | 960 | 0.21 | 4570 | 3030 | 25 |

[a]A unit was the amount of enzyme required to catalyze the reduction of 2 mmol DTNB (or 1 mmol of CoA disulfide) in 1 min.

As shown in Table 2, the primary purification step was the 2',5'-ADP-Sepharose affinity chromatography, which provided a 300-fold purification. 2',5'-ADP mimics NADPH, the enzyme's natural substrate for which it has micromolar affinity (see, Table 3). CoADR from the ADP column was contaminated by three other proteins that were easily removed by MonoQ anion exchange chromatography. CoADR activity eluted in two peaks. The second peak had a higher specific activity than the first and was the only fraction retained for further study. SDS-PAGE followed by silver staining of this fraction shows that it is greater than 95% homogeneous. All subsequent physical and chemical characterizations were performed on this sample.

B. DETERMINATION OF CoADR NATIVE MOLECULAR WEIGHT.

The native molecular weight of CoADR was estimated by gel exclusion chromatography. A sample of the purified CoADR from the monoQ column (0.5 ml) was loaded onto a sepharose 6 HR 10/30 gel exclusion column (Pharmacia, 25 ml) (0.5 ml/min) equilibrated in Tris-HCl (20 mM), pH 8.0, containing NaCl (1 M) and then eluted isocratically in the same buffer. Fractions containing CoADR were identified by UV absorbance and activity measurements. The native molecular weight of CoADR was estimated by extrapolation of the parameter K from a standard plot of K versus the log of the molecular weight of protein standards. The parameter, K, is defined as $(V_e-V_o)/V_s$ where $V_e$ is the volume of solvent required to elute the protein of interest, $V_o$ is the void volume or the volume of solvent required to elute a totally excluded protein, and $V_s$ is the volume of the stationary phase as determined by the subtraction of the void volume from the total volume of the column. Freifelder (1976) *Physical Biochemistry* (W.H. Freeman and Company. New York).

Purified CoADR migrates as a single polypeptide of ~50 kD apparent molecular weight according to SDS-PAGE. Native CoADR elutes between 44 and 158 kD from the superose gel filtration column. The K value calculated for CoADR (0.5) can be extrapolated to a molecular weight of approximately 85 kD. This suggests that CoADR is a homodimer in its native state.

C. FLAVIN COFACTOR IDENTIFICATION.

The absorbance spectrum of purified CoADR is that of a typical flavoenzyme, having maxima at 454 and 360 nm. To identify the apparently bound flavin, purified CoADR was denatured, and the migration of the released cofactor on a reverse phase HPLC was compared to that of riboflavin, FMN, and FAD. A sample (0.1 ml) of CoADR (10 mM) was heated to 95° C. for 10 min and then centrifuged (17,000×g, 10 min) to remove the denatured protein. The supernatant was then separated by reverse phase HPLC. Sundquist et al. (1989) *J. Biol. Chem.* 264:719–725.

The visible absorbance spectrum of purified CoADR is typical of that of a flavoenzyme. The enzyme has a $l_{max}$ at 450 nm and 360 nm. Boiled and centrifuged CoADR demonstrated no detectable CoADR activity and was not observable on an SDS-PAGE gel. The sample maintained the absorbance spectra of a flavin, suggesting that boiling had released the cofactor and centrifugation had removed the denatured protein. A chromatograph of the flavin sample separated by reverse phase HPLC showed that the flavin from CoADR migrates the same as FAD and elutes much later than either riboflavin or FMN. Thus, CoADR is a flavoenzyme utilizing a non-covalently bound FAD as cofactor. Quantitation of the flavin released from CoADR reveals that 1 flavin molecule is released per subunit of enzyme denatured.

D. THIOLS/ACTIVE SITE.

To determine if CoADR utilized catalytic cysteine residues, a thiol titration of the active site was performed. A solution of oxidized CoADR (9.5 mM) in TE was incubated with NADPH (0.2 mM) for 10 min at ambient temperature before being diluted (1:1) with TE containing 8 M urea and DTNB (0.2 mM). The absorbance at 412 nm was then measured and compared to that of a similar reaction in which CoADR was not incubated with NADPH. The number of thiols liberated per FAD was then calculated.

Thiols are the most reactive nucleophiles in the cell. mBB is a very reactive electrophile and reacts with most cellular nucleophiles. NEM, however, is less reactive and more selective for thiols. NEM pretreatment of a sample thus selectively modifies thiols so that they do not react with mBB. Thiols are thus identified as peaks appearing in the mBB treated sample but not in the NEM pretreated sample. S. aureus produces predominantly CoA, $H_2S$, and a small amount of cysteine. 3'-Dephosphorylation of CoA occurs under the acidic conditions of the HPLC protocol, so CoA is determined by the combined peaks of CoA and 3'-dephospho-CoA. The majority of $H_2S$ presumably originated from FeS proteins. A large peak running at 18 minutes has been previously isolated and characterized as bismethylbimane. This compound apparently arises from the demethylation of mBB by some cellular factor. No GSH was detected.

Reduction of CoADR with NADPH liberated 3.2±0.2 thiols/subunit (according to FAD concentration), while 0.9±0.2 thiol was detected in the denatured enzyme that was not incubated with NADPH. This suggests that CoADR in its oxidized state has one reduced cysteine, likely buried in its core, and that upon reduction with NADPH a disulfide bond involving at least one enzymic cysteine is reduced. Thus, CoADR likely utilizes a thiol-disulfide exchange mechanism in its reduction of CoA disulfide. While this is suggestive of an active site having two cysteine residues, it only demonstrates that incubation with NADPH results in the reduction of a disulfide bond involving at least one enzymic thiol. Indeed, CoADR utilizes only a single active site cysteine, which in the oxidized enzyme forms a mixed disulfide with CoA.

E. $Cu^{2+}$ CATALYZED OXIDATION OF CYSTEINE, GSH, AND CoA.

To determine the relative stability of CoA to heavy metal-catalyzed oxidation, the rate of $Cu^{2+}$ catalyzed oxidation of cysteine, GSH, and CoA were compared. Each sample (2 ml) of thiol (1 mM) in Tris-HCl buffer (20 mM), pH 7.5, containing $CuCl_2$ (1 mM) was incubated at ambient temperature. Thiol determination was then carried out at various times by adding aliquots (100 ml) from each sample to a solution (900 ml) of DTNB (1 mM) in Tris-HCl buffer (20 mM), pH 8.0, containing EDTA (1 mM). The absorbance of these samples at 412 nm was measured and the concentration of remaining thiol determined.

Although cysteine is necessary for all cells, it is rarely the predominant cellular thiol, especially in aerobic organisms. This is believed to be because cysteine undergoes rapid metal catalyzed autooxidation when exposed to oxygen to produce cystine and hydrogen peroxide.

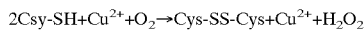

$$2Csy\text{-}SH + Cu^{2+} + O_2 \rightarrow Cys\text{-}SS\text{-}Cys + Cu^{2+} + H_2O_2$$

Glutathione provides a reserve of cysteine which is much more stable to metal catalyzed oxidation. Although CoA would not be an efficient storage form of cysteine, as the predominant thiol in S. aureus it should be resistant to metal-catalyzed oxidation. Cys, GSH, and CoA each show a different rate of copper-catalyzed autooxidation. Cysteine is the least stable to oxidation. CoA and GSH are of comparable stability and are much more stable than cysteine. The high concentrations of CoA in S. aureus thus represent a stable thiol buffer analogous to that provided by GSH in other organisms.

F. KINETIC CHARACTERIZATION OF CoADR SUBSTRATE SPECIFICITY.

CoADR is specific for CoA disulfide and NADPH. The specificity of CoADR for these substrates and various other biological disulfides were quantitated kinetically. Kinetic measurements were performed in a 1 cm path-length quartz cuvette maintained at 37° C. Each assay (0.3 ml) was carried out in buffer A containing CoADR (2–10 nM), NADPH (2–200 μM), and either CoA disulfide (2–200 μM), 3'-dephospho-CoA disulfide (10–500 μM), 4,4'-diphospho-pantethine (2–400 μM), pantethine (10 μM–100 mM), glutathione disulfide (10 μM–100 mM), cystine (10 μM–100 mM), and CoA-glutathione mixed disulfide (10 μM–100 mM). Enzyme and NADPH were combined in buffer and equilibrated to 37° C., and the reaction was initialized by the addition of the disulfide substrate. The activity of CoADR was monitored at 340 nm as the decrease in absorbance resulting from the oxidation of NADPH. All kinetic measurements were recorded in the linear range, and at least seven substrate concentrations were used for each analysis. Kinetic constants were calculated from a linear least squares fit of the initial velocity data to the Michaelis-Menton equation using the program HyperO. Cleland (1979) Meth. Enzymol. 63:103–138. The results of this analysis are shown in Table 3.

A variation of the pH between 6.0 and 9.0 at constant NADPH and CoA disulfide concentrations, showed that CoADR has an optimal operating pH of 7.5–8.0. CoADR is very specific for its physiological substrates CoA disulfide and NADPH and is saturated by micromolar concentrations of each. The $K_m$ for NADPH, at saturating CoA disulfide, was 2 μM and the $K_m$ for CoA disulfide, at saturating NADPH, was 11 μM. Table 3 shows the results of the kinetic analysis of the CoADR catalyzed reduction of various disulfide substrates by NADPH.

TABLE 3

Steady state kinetic analysis of the oxidation of NADPH by various disulfide substrates catalyzed by S. aureus coenzyme A disulfide reductase.[a]

| Substrate | $k_{cat}$ (min$^{-1}$) | $K_m$ (μM) | $k_{cat}/K_m$ (M$^{-1}$s$^{-1}$) × 10$^6$ |
|---|---|---|---|
| NADPH | 1020 ± 60 | 1.6 ± 0.5 | 600 ± 100 |
| CoA disulfide | 1000 ± 200 | 11 ± 2 | 80 ± 10 |
| 3'-dephospho-CoA disulfide | 1400 ± 200 | 140 ± 40 | 10 ± 2 |
| 4,4'-diphospho-pantethine | 540 ± 40 | 80 ± 10 | 3.3 ± 0.4 |
| pantethine | nd | nd | nd |
| CoASSG | 800 ± 70 | 1100 ± 200 | 0.72 ± 0.08 |
| cystine | nd | nd | nd |
| GSSG | nd | nd | nd |

[a]CoA disulfide was maintained at 120 mM to determine the kinetic parameters for NADPH, and NADPH was maintained at 200 mM for the disulfide substrates.
nd = no activity detected.

A selective deletion of the chemical moieties that make up CoA has provided some insight to their contribution to the binding and turnover of CoA disulfide. Since hydride transfer from NADPH has been shown to be rate limiting for those pyridine nucleotide-dependent disulfide reductases investigated to date, it is not surprising that the $k_{cat}$ values for each of the substrates are similar. The 3'-phosphate moieties contribute predominantly to ground state binding (~1.5 kcal), resulting in a 10-fold increase in $K_m$ with no detectable change in $k_{cat}$ for 3'-dephospho-CoA disulfide as compared to CoA disulfide. It is interesting that the $K_m$ for the 4,4'-diphosphopantethine is similar to the 3'-dephospho- CoA disulfide but that the $k_{cat}$ is 2–3 fold lower. Thus, the adenyl moiety does not appear to contribute to ground state binding, but rather to transition state binding. In addition, the low $k_{cat}$ for the 4,4'-diphosphopantethine suggests that disulfide reduction may be rate limiting for this substrate. Since pantethine is not turned over by CoADR, the 4- and 4'-phosphate moieties are clearly essential for substrate binding and turnover. Interestingly, CoADR did act on CoASSG although with a high $K_m$=1.1 mM. No activity could be detected for GSSG or cystine.

EXAMPLE 3

Recombinant Production of *S. aureus* CoADR

The gene encoding *S. aureus* CoADR was isolated and sequenced using methods described below. Generally, the gene was identified by PCR using degenerate primers shown in Table 4A based on the N-terminal sequence of CoADR and an internal amino acid sequence of the enzyme shown in Table 4B. The DNA fragment generated by the PCR was labeled and used as a probe in the isolation of a 4.5 kB HindIII fragment from *S. aureus* genomic DNA that carried the cdr gene. The sequence of the open reading frame and the deduced amino acid sequence are shown in FIG. 1 and FIG. 2, respectively.

TABLE 4A

Degenerate oligonucleotide primers used in the PCR amplification of an internal region of the gene encoding CoADR

| Oligomer | Sequence |
| --- | --- |
| SD-111 (N-terminal region) | 5'-GG(AT)GC(AT)GT(ACT)GC(AT)GG(AT)GG(AT)GC-3' (SEQ ID NO:4) |
| SD-113 (internal region) | 5'-AAG(AT)G(CA)AAATAG(AG)TTAATAG(AG)TT(AT)AT(AT)CCAAC-3' (SEQ ID NO:5) |

TABLE 4B

Degenerate oligonucleotide primers used in the PCR amplification of an internal region of the gene encoding CoADR

| Region | Sequence |
| --- | --- |
| N-terminal Peptide | PPKIVVVGAVAGGAT (SEQ ID NO:6) |
| Internal Peptide | NQPILDESDKREIPYP (SEQ ID NO:7) |

Identification of a DNA Fragment Encoding the N-terminal of CoADR—CoADR was purified as described in Example 2. CoADR and CoADR cleaved with cyanogen bromide, Matsudaira (1990) *Meth. Enzymol.* 182:602–613, were separated by SDS-PAGE, blotted onto Immobilon PVDF membrane (Millipore), and visualized with coomasie blue staining (in the absence of acetic acid). The bands corresponding to native CoADR and a 35 kD CNBr cleavage product were excised and submitted for N-terminal sequencing to the Protein Sequencing Laboratory of the University of Victoria (Victoria, British Columbia). The N-terminal amino acid sequences of the native CoADR and of the 35 kD CNBr-cleavage product are shown in Table 4B.

Degenerate oligonucleotides, which were designed to encode the N-terminal (coding) and internal (non-coding) sequences, were used as primers for the PCR of *S. aureus* genomic DNA. The PCR reaction contained 10 ng genomic DNA, 100 pmol each of 5'-GG(AT)GC(AT)GT(ACT)GC(AT)GG(AT)GG(AT)GC-3' (SEQ ID NO:4) and 5'-AAG(AT)G(CA)AAATAG(AG)TTAATAG(AG)TT(AT)AT(AT)CCAAC-3' (SEQ ID NO:5), MgCl$_2$ (2.4 mM), tetramethyl ammonium chloride (Sigma) (60 mM), deoxynucleotide triphosphates (dNTPs) (0.25 mM of each), and 1× PCR buffer (Gibco BRL). The reaction was incubated at 95° C. (30 sec), 47° C. (30 sec), and 72° C. (30 sec) for 30 cycles. The resulting 600 bp PCR product was cloned directly using a TA cloning kit (Invitrogen) and sequenced using the universal "forward" and "reverse" primers which are homologous to the flanking region of the multiple cloning site within the plasmid pCR II (the TA cloning vector (Invitrogen)).

Cloning and Sequencing of the Gene Encoding CoADR—The cloned PCR fragment encoding the N-terminal of CoADR was excised from the TA cloning vector by digestion with EcoRI and band purified from an agarose gel. The fragment was labeled with digoxygenin and used to probe Southern blots of *S. aureus* genomic DNA digested with various restriction enzymes. A single 4.5 kB HindIII fragment that hybridized to the probe under stringent conditions (68° C., 0.1 SSC buffer containing 0.1% SDS) was subcloned into plasmid pUC18 and sequenced. Initial sequencing primers were designed to prime within the sequence of the PCR fragment described above and to sequence into the flanking region. New primers were designed within the new sequences and the nucleotide sequence of the entire gene was thus determined stepwise. All of the sequences were confirmed by sequencing both the coding and noncoding strands.

Heterologous Overexpression of CoADR in *E. coli*—The open reading frame encoding CoADR was amplified by the PCR using the N-terminal PCR primer GGGAATTCCATATGCCCAAAATAGTCGTAGTCGG, (SEQ ID NO:8), and the C-terminal PCR primer CCCAAGCTTTATTTAGCTTTGTAACCAATCAT (SEQ ID NO:9). The resulting fragment was digested with NdeI and HindIII, purified, and ligated with pET22B(+) (Novagen, Madison Wis.) that had been digested with the same two enzymes and purified similarly to produce plasmid pCDRX. An overnight culture (10 mL) of *E. coli* BL21 (DE3) cells harboring pCDRX was washed twice in 10 mL of TB medium, and used as an inoculum for 1 liter of the same medium containing ampicillin (400 mg/mL). The resulting culture was incubated at 37° C. until it reached mid-stationary phase ($A_{600\ nm}$=1.2), induced to express recombinant CoADR (rCoADR) by the addition of IPTG (to 1 mM), and then incubated for an additional 3 hours at 37° C. The cells were harvested and the recombinant enzyme was purified as described in Example 1 for native CoADR except that lysozyme (2 mg/mL) was used in place of lysostaphin to assist in disrupting the cells. The purity of the resulting recombinant enzyme was measured by SDS-PAGE and staining with brilliant blue. The specific activity and purity from *E. coli* glutathione reductase was measured spectrophotometrically by following the oxidation of NADPH calorimetrically. This procedure allows for the recovery of approximately 10 mg/mL of rCoADR from the soluble fraction of the cell lysate that is >98% pure and free of glutathione reductase activity.

Gene Inactivation—A cdr⁻ strain of *S. aureus*, strain RN4220, was created by the recombination of a plasmid carrying an internal fragment of the cdr gene into the RN4220 chromosome by Cambell-like integration. The resultant mutant formed small colonies on TSA plates and had less than 10% recovery from starvation conditions.

EXAMPLE 4

Identification of Genes Encoding CoADR in *Staphylococcus epidermidis, Enterococcus faecalis* and *Enterococcus faecium*

The polypeptide sequence of CoADR from *S. aureus* shown in FIG. 2 (and designated hereinafter as Cdr_Sa) was used to search for genes having similar or identical sequences (and thus theoretically the same functional activity as *S. aureus* CoADR) in a variety of microorganisms. The database search tool BLAST (Altschul, S. F., Gish, W., Miller, W., Myers, E. W., Lipman, D. J. J. Mol. Biol. 215:403–410, 1990) was employed to search the PathoSeq™ database, version 2.0 (Incyte Pharmaceuticals, Palo Alto, Calif.). Significant matches were found in the genomic sequences of three organisms, *Staphylococcus epidermidis* O-47 (available from Incyte), *Enterococcus faecalis* ATCC 29212 (available from the American Type Culture Collection, 12301 Parklawn Dr., Rockville, Md. 20852) and *Enterococcus faecium* BM1447-1 (also available from Incyte), specifically in four contiguous sequences (contigs) designated SEP1c0373, EFA1c0950, EFM1c0384, and EFM1c06857, respectively. The open reading frame encoding CoADR in each contig was identified and the corresponding polypeptide product deduced. The genes for CoADR in *S. epidermidis* (designated cdr_Se), *E. faecalis* (cdr_Efa), and *E. faecium* (cdrA_Efm and cdrB_Efm), and their corresponding polypeptides (Cdr_Se, Cdr_Efa, CdrA_Efm and CdrB_Efm, respectively) are shown in FIGS. 3–6.

EXAMPLE 5

Cloning of the *S. epidermidis* CoADR Gene and Overexpression in *E. coli*

The open reading frame encoding the polypeptide Cdr_Se is amplified by PCR from genomic DNA of *S. epidermidis* O-47 using the N-terminal primer 5'-GGCCCTCTAGAAATAATTTTGTTTAACTTTAAGAAGGAGATATACATATGAATAAAATTATAATAGTCGGTG-3' (SEQ ID NO:21) and the C-terminal reverse primer 5'-CCCAAGCTTTATTGCGCTTTATACCCAATTAA-3' (SEQ ID NO:22). The resulting amplified fragment is digested with the enzymes XbaI and HindIII and ligated with the vector pET22B(+) digested with the same enzymes. The resulting plasmid, designated pCDRSE, is introduced in *E. coli* BL21 (DE3) essentially as in Example 3, subsection "Heterologous overexpression of CoADR in *E. coli*." The *E. coli* strain carrying pCDRSE is grown and the Cdr_Se enzyme is isolated essentially as described in Example 3 (Heterologous overexpression of CoADR in *E. coli*) and analyzed as in Example 1.

EXAMPLE 6

Cloning of the *E. faecalis* CoADR Gene and Overexpression in *E. coli*

The open reading frame encoding the polypeptide Cdr_Efa is amplified by PCR from genomic DNA of *E. faecalis* ATCC 29212 using the N-terminal primer 5'-GGGAATTCCATATGAAAATTGTAATTATCGGAGG-3' (SEQ ID NO:23) and the C-terminal reverse primer 5'-CCCAAGCTTTTATACATTTTCTAGTTCCTCCG-3' (SEQ ID NO:24). The resulting amplified fragment is digested with the enzymes NdeI and HindIII and ligated with vector pET22B(+) digested with the same enzymes to produce the plasmid designated pCDREF. Plasmid pCDREF is introduced in *E. coli* BL21 (DE3) essentially as described in Example 3. The *E. coli* strain carrying pCDREF is grown and the Cdr_Efa enzyme isolated (as in Example 3) and analyzed as in Example 1 with the modification that both NADPH and NADH are added to the reaction mixtures at 0.1 mM each.

EXAMPLE 7

Cloning of the *E. faecium* cdrA Gene and Overexpression in *E. coli*

The open reading frame encoding the polypeptide Cdr_Efm is amplified by PCR from genomic DNA of *E. faecium* BM4147 using the N-terminal primer 5'-GGGAATTCCATATGAAAATCGTTATTGTCGG-3' (SEQ ID NO:25) and the C-terminal reverse primer 5'-CCCAAGCTTTCATTTGTTAGGATATATCAG-3' (SEQ ID NO:26). The resulting amplified fragment is digested with the enzymes NdeI and HindIII and ligated with the vector pET22B(+) digested with the same enzymes to produce the plasmid designated pCDREMA which is introduced in *E. coli* BL21 (DE3) essentially as described in Example 3. The *E. coli* strain carrying pCDREMA is grown and the CdrA_Efm enzyme is isolated and analyzed as described in Example 6.

EXAMPLE 8

Cloning of the *E. faecium* cdrB Gene and Overexpression in *E. coli*

The open reading frame encoding the polypeptide CdrB_Efm is amplified by PCR from genomic DNA of *E. faecium* BM4147 using the N-terminal primer 5'-GGGAATTCCATATGAAAGTTGTTGTCATTGG-3' (SEQ ID NO:27) and the C-terminal reverse primer 5'-CCCAAGCTTTTATTCTTCAATCAAAACCG-3' (SEQ ID NO:28). The resulting amplified fragment is digested with the enzymes NdeI and HindIII and ligated with the vector pET22B(+) digested with the same enzymes to produce the plasmid designated pCDREMB. Plasmid pCDREMB is introduced in *E. coli* BL21 (DE3) essentially as described in Example 3. The *E. Coli* strain carrying pCDREMB is grown and the CdrB_Efm enzyme is isolated and analyzed as described in Example 6.

EXAMPLE 9

Inactivation of cdr_Se

A 700 bp segment internal to cdr_Se, corresponding to nt 201–900, is amplified by PCR employing the primers 5'-GGGAATTCGATTATGACAAAAAGCAAATCA-3' (SEQ ID NO:29) which contains an EcoRI site near the 5' end and 5'-GGTTCGAATAACGGTGTGCTCCCCAAGCAA-3' (SEQ ID NO:30) which contains a HindIII site. The amplified fragment is digested with the enzymes EcoRI and HindIII and then ligated into the vector pAUL-A (described by Schaeferkordt, S.; Chakraborty, T. 1995. Biotechniques 19:720–722) which is digested with the same enzymes. The resulting plasmid, designated pCDRSE-int is introduced in E. coli. The E. coli strain carrying pCDRSE-int is grown and harvested and the plasmid pCDRSE-int isolated. The plasmid is electroporated into S. epidermidis following the procedures described in Augustin, J; Goetz, F. 1990. FEMS Microbiol. Lett. 66:203–208. employing selection for erythromycin resistance. A culture of S. epidermidis/pCDRSE-int is grown to mid log phase in the presence of erythromycin then plated on TSA plates containing erythromycin. To verify that the inactivated cdr_Se is an essential gene, the plates are incubated at 45° C. and the surviving colonies (carrying pCDRSE-int integrated in the cdr_Se gene) are examined for colony size and extent of growth. Poor growth and small sized colonies indicate that cdr_Se is an essential gene.

EXAMPLE 10

Inactivation of cdr_Efa

A 700 bp segment internal to cdr_Efa, corresponding to nt 201–900, is amplified by PCR employing the primers 5'-GACCGGATCCGTTTAATTTAGATGTTCG-3' (SEQ ID NO:31) and 5'-GACCGGATCCGCGATTGGCAGGAG (SEQ ID NO:32) which contain a BamHI site near the 5' end. The amplified fragment is digested with BamHI and ligated with the plasmid pACYC184 which is digested with the same enzyme. The resulting plasmid, designated pCDREF-int, is introduced in E. coli. The E. coli strain carrying pCDREF-int is grown and harvested and the plasmid pCDREF-int is isolated and electroporated into E. faecalis ATCC29212 following the method of Cruz-Rodz, A.; Gilmore, M. 1990. Mol. Gen. Genet. 224:152–154 employing selection for chloramphenicol resistance. To verify that cdr_Efa as an essential gene, the drug resistant colonies are grown on rich medium and as in Example 9, examined for colony size and extent of growth.

EXAMPLE 11

Inactivation of cdrA_Efm

A 720 bp segment internal to cdrA_Efm, corresponding to nt 181–900, is amplified by PCR employing the primers 5'-GACCGGATCCCAAACGCCAGAATCATTATTCG-3' (SEQ ID NO:33) and 5'-GACCGGATCCGGCTGGTGAAGCAAGAG (SEQ ID NO:34) each of which contain a BamHI site near the 5' end). The amplified fragment is digested with BamHI and ligated with the plasmid pACYC184 which is digested with the same enzyme. The resulting plasmid, designated pCDREMA-int, is introduced in E. coli. The E. coli strain carrying pCDREM-int is grown and harvested and the plasmid pCDREMA-int is isolated and electroporated into E. faecium BM4147 following the method of Cruz-Rodz, A.; Gilmore, M. 1990. Mol. Gen. Genet. 224:152–154 employing selection for chloramphenicol resistance. Verification of cdrA_Efm as an essential gene is performed as described in Example 10.

EXAMPLE 12

Inactivation of cdrB_Efm

A 720 bp segment internal to cdrB_Efm, corresponding to nt 181–900, is amplified by PCR employing the primers 5'-GAGGGAATTCAGTTGTGCTTTGCCTTATTATTTAG-3' (SEQ ID NO:35) and 5'-GAGGGAATTCGGAAAGCATACTTTGG-3' (SEQ ID NO:36) each of which contain an EcoRI site near the 5' end. The amplified fragment is digested with EcoRI and ligated with the plasmid pACYC184 which is digested with the same enzyme. The resulting plasmid, designated pCDREMB-int, is introduced in E. coli. The E. coli strain carrying pCDREMB-int is grown and harvested and the plasmid pCDREMB-int is isolated and electroporated into E. faecium BM4147 following the method of Cruz-Rodz, A.; Gilmore, M. 1990. Mol. Gen. Genet. 224:152–154 employing selection for tetracycline resistance. Verification of cdrB_Efm as an essential gene is performed as described in Example 10.

EXAMPLE 13

Cloning of cdr-homologous Genes from Bacteria using Consensus Primers

An alignment of the Cdr polypeptide sequences from S. aureus, S. epidermidis, E. faecalis, and E. faecium is shown in FIG. 7. The consensus sequences FA(N/S)C (aa 40–43, SEQ ID NO:37) and Y(A/S)PP (aa 427–430, (SEQ ID NO:38) are chosen from which oligo nucleotide PCR primers are made. The primer for the FANC sequence is 5'-TT (T/C)GAIAA(U/C)UG(U/C) [I=inosine] (SEQ ID NO:39) which has 8-fold degeneracy. The reverse primer for the YAPP sequence is 5'-AIGGIGGIGC(A/G)TA (SEQ ID NO:40). The reverse primer carries 2-fold degeneracy. The A on the 5' end of the reverse primer represents the complement of the T on the 5' end of the codons TT(T/C) and TA(T/C) for phenylalanine and tyrosine, which follow the YAPP sequence in the staphylococci and enterococci CoADR proteins, respectively. The primers are used in a PCR experiment with genomic DNA isolated from a bacterium from which the cdr-homologous sequence is desired. This may be done with a single organism or with a group of organisms mixed together. Genomic DNA is isolated as described in general methods or in Sambrook, J. et al., 1989, supra. A PCR amplified fragment of approximately 1.2 kb is identified after agarose gel electrophoresis. The fragment is purified and its nucleotide sequence is examined and shown to have at the protein level, at least 30% identity to amino acids 40–440 of the S. aureus CoADR shown in FIG. 7. The fragment is then used as a hybridization probe against the genomic DNA of the bacterium from which it was isolated to identify the complete (cdr-homologous gene. Hybridization can be performed with total genomic DNA digested with a variety of enzymes in a Southern blot experiment or by colony or plaque hybridization with a genomic library from the organism in a plasmid, cosmid or phage propagated in E. coli. Once the genomic sequence is identified, it can be sub-cloned in pET22B(+) or another vector as described in Example 3 to yield purified Cdr protein.

EXAMPLE 14

Cloning of cdr-homologous Genes from Bacteria using Mixed Probes

Approximately 5 μg of the PCR-generated amplified sequences of the CoADR genes from S. aureus, S. epidermidis, E. faecalis and E. faecium, prepared as described in Examples 3, 5, 6, 7 and 8 are mixed together, diluted appropriately and used (as a single or mixed probe) in a hybridization experiment with total genomic DNA prepared from a desired bacterium or from a mixture of bacteria as described in Example 13. Hybridization can be performed by Southern blot or by colony or plaque hybridization with a genomic library from the organism or organisms in a plasmid, cosmid or phage propagated in E. coli. Once the genomic sequence is identified, it can be subcloned in pET22B(+) or another vector as described in Example 3 to yield purified Cdr protein.

EXAMPLE 15

High Throughput Assay to Identify Inhibitors of CoADR

100 μl of a reaction mixture containing 50 mM Tris-HCl, pH 7.8, 50 mM NaCl, 50 μM NADPH, 100 μM Coenzyme A disulfide (CoAS-SCoA) and 100 μM DTNB (Ellman's Reagent) is added to all the wells of a series of a 96 well microtiter plate. Wells 1 through 94 also contain one of the following: a few μg of a single compound either as a dry powder or in 1–5 μl of 50 mM Tris-HCl, pH 7.8, 50 mM NaCl buffer; a few μg each of a mixture of compounds either as a dry powder or in a few μl of 50 mM Tris-HCl, pH 7.8, 50 mM NaCl buffer; uncharacterized mixtures of compounds extracted from bacteria, fungi, plants, marine organisms or other organisms in a few μl of water, buffer, or DMSO. In the first two cases, the amounts of compound employed is adjusted so that after all the additions are made, the concentration of each compound is in the range of 1–10 μM. Wells 95 and 96 do not contain compound or extract. To wells 1–95 is added 0.01 units of purified CoADR from S. aureus, S. epidermidis or E. faecalis. A unit of enzyme is defined as the amount that can oxidize 1 μmole of reduced pyridine nucleotide per minute. Well 96 is left as the no enzyme control. The plates are incubated for 30 min at room temperature and the reactions are then stopped in each well by the addition of 100 μl of 0.2% sodium dodecyl sulfate. The absorbance at 412 nm is read in each well. This entire process may be scaled up to many microtiter plates with the help of robots, automated plate readers, multichannel pipetters, etc.

The net well 95 absorbance is determined by subtracting the background absorbance in well 96 from the absorbance in well 95, the uninhibited enzyme. The absorbances determined for wells 1–94 are compared against net well 95 absorbance. Wells which show less than 50% of the absorbance relative to net well 95 are considered potential "hits". The compound(s) or extracts in the wells are then reexamined in a number of duplicate assays using the CoADR enzymes from S. aureus, S. epidermidis and E. faecalis to confirm the initial results and to determine the IC50 or $K_i$ values for the various inhibitors.

In the preceding examples, the plasmid pAUL-A, is employed to perform the gene disruptions in Staphylococcus aureus and Staphylococcus epidermidis. It is understood by those skilled in the art that other plasmids, such as pE194ts (Villafane, R.; Bechofer, D.; Narayanan, C.; Dubnau, D. 1987. J. Bacteriol. 169:4822–4829) can be used in place of pAUL-A to perform gene disruptions in cdr genes. These temperature-sensitive plasmids replicate in staphylococci at low temperature but do not replicate at high temperature.

In Examples 10, 11 and 12, the plasmid pACYC184, which carries the selectable markers for chloramphenicol and tetracycline resistance in both Gram negative and Gram positive bacteria is used for peforming a gene disruption experiment in the cdr genes in E. faecalis and E. faecium. It is understood that gene inactivation in the enterococci may be performed with a plasmid incapable of replication in Enterococcus sp. but which carries a marker for selection in enterococci, as described by Nakayama, J, et al. 1995. FEMS Microbiol. Letters 128:283–285. Thus any plasmid into which an internal segment of cdr_Efa, cdrA_Efm or cdrB_Efm can be placed, including but not limited to pUC18, pUC19, pBR322 and pET22B(+), and which carries a marker selectable in E. faecalis or E. faecium, including but not limited to chloramphenicol resistance, erythromycin resistance and tetracycline resistance, can be used in place of pACYC184 to inactivate cdr_Efa, cdrA_Efm or cdrB_Efm.

Furthermore, although a process to inactivate the cdr genes by gene disruption employing homologous recombination was exemplified herein (Examples 9–12), it is understood that other ways to inactivate genes exist. These include, but are not limited to CoADR inactivation by insertion of transposons in cdr genes or replacement of all or part of a cdr gene with a sequence not encoding the CoADR function. Thus all methods to inactivate the CoADR function by genetic manipulation of the corresponding cdr gene are included within the scope of the invention. In addition, although methods are described herein (Examples 11 and 12) to inactivate each of the cdr genes present in E. faecium separately, it is understood that any of the survivors of a disruption of cdrA can be used for disruption of cdrB as described in Example 12. Conversely, a survivor of a disruption of cdrB can be used for disruption of cdrA as described in Example 12. It is understood, however, by those skilled in the art that if the same vector is used in the two sequential cdr disruption experiments in E. faecium, it is possible that in a strain carrying an integrated sequence of pACYC184 in its host genome, the incoming pACYC184 plasmid carrying a portion of the second cdr gene to be disrupted may undergo homologous recombination with its cognate sequence in the chromosome. Thus, recombinants that carry the two selection markers must be checked by Southern hybridization to ensure that integration is in the intended cdr gene. The necessity of confirming proper integration may be avoided by using a different vector for each disruption.

Another method commonly used to identify genes, expression cloning, can also be used to identify cdr genes in bacteria. Purified CoADR from any of the four organisms decribed herein can be injected into rabbits or other animals for the purpose of raising antibodies which can subsequently be used to detect clones of bacteria or phage into which genes from heterologous sources have been cloned and which express a protein which will react with the antibody. DNA from such clones of bacteria or phage can then be examined directly by methods described herein to identify the DNA and subsequently the corresponding polypeptide for CoADR activity. Thus, methods to identify cdr genes through use of an antibody raised against a known or presumed CoADR protein are included within the scope of the invention.

In Example 15, a high throughput assay to identify inhibitors of CoADR is described employing a microtiter assay and the use of robots, automated readers, etc. It is understood by those skilled in the art that there are many formats available to screen for enzyme inhibitors, including 96 well and 256 well microtiter plates, high density racks of tubes, etc. as well as different formats of robotic apparati. All formats used to screen for inhibitors of CoADR are, therefore, included in the scope of this invention. In addition, whereas reduction of DTNB by CoASH (absorbance at 412 nm) was used to assay for activity of CoADR, direct assay for oxidation of NADPH (change in absorbance at 340 nm) can also be used to monitor enzyme activity. Furthermore, whereas SDS was exemplified herein to terminate the CoADR-mediated reaction, it is understood that many procedures or reagents can be used to stop enzyme-mediated reactions including but not limited to raising or lowering the temperature or adding acid, base, solvents, chaotropic agents or detergents. Thus any procedure or reagent that is used to terminate the reaction employed to screen for inhibitors of CoADR that does not change or interfere with the detection system employed is included within the scope of this invention. In addition, whereas individual compounds or groups of compounds selected from a compound library for the screening for inhibition of CoADR are exemplified herein, it is understood that many variations of chemical compounds can be used to screen for CoADR inhibition, including but not limited to compounds derived from natural products, compounds synthesized combinatorially, etc. Any compound produced that can be tested for inhibition of CoADR is included under the scope of this invention. Furthermore, whereas addition of the enzyme to the reaction tubes carrying putative inhibitors to initiate the reactions was exemplified herein, it is understood that the assay can be reformatted to allow some time for the potential inhibitor to interact with the enzyme before the reaction is initiated, for example by adding the substrate CoA disulfide. Thus all formats to assay for inhibition of CoADR are included within the scope of the invention.

Although preferred embodiments of the subject invention have been described in some detail, it is understood that obvious variations can be made without departing from the spirit and the scope of the invention as defined by the appended claims.

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
      (A) LENGTH: 1317 base pairs
      (B) TYPE: nucleic acid
      (C) STRANDEDNESS: double
      (D) TOPOLOGY: linear (ii) MOLECULE TYPE: Genomic DNA (xi) SEQUENCE DESCRIPTION: SEQ ID NO:1:

```
ATGCCCAAAA TAGTCGTAGT CGGAGCAGTC GCTGGTGGTG CAACATGTGC CAGCCAAATT      60

CGACGTTTAG ATAAAGAAAG TGACATTATT ATTTTTGAAA AAGATCGTGA TATGAGCTTT     120

GCTAATTGTG CATTGCCTTA TGTCATTGGC GAAGTTGTTG AAGATAGAAG ATATGCTTTA     180

GCGTATACAC CTGAAAAATT TTATGATAGA AAGCAAATTA CAGTAAAAAC TTATCATGAA     240

GTTATTGCAA TCAATGATGA AAGACAAACT GTATCTGTAT TAAATAGAAA GACAAACGAA     300

CAATTTGAAG AATCTTACGA TAAACTCATT TTAAGCCCTG GTGCAAGTGC AAATAGCCTT     360

GGCTTTGAAA GTGATATTAC ATTCACACTT AGAAATTTAG AAGACACTGA TGCTATCGAT     420

CAATTCATCA AAGCAAATCA AGTTGATAAA GTATTGGTTG TAGGTGCAGG TTATGTTTCA     480

TTAGAAGTTC TTGAAAATCT TAATGAACGT GGTTTACACC CTACTTTAAT TCATCGATCT     540

GATAAGATAA ATAAATTAAT GGATGCCGAC ATGAATCAAC CTATACTTGA TGAATTAGAT     600

AAGCGGGAGA TTCCATACCG TTTAAATGAG GAATTAATG CTATCAATGG AAATGAAATT      660

ACATTTAAAT CAGGAAAAGT TGAACATTAC GATATGATTA TTGAAGGTGT CGGTACTCAC     720

CCCAATTCAA AATTTATCGA AAGTTCAAAT ATCAAACTTG ATCGAAAAGG TTTCATACCG     780

GTAAACGATA AATTTGAAAC AAATGTTCCA AACATTTATG CAATAGGCGA TATTGCAACA     840

TCACATTATC GACATGTCGA TCTACCGGCT AGTGTTCCTT TAGCTTGGGG CGCTCACCGT     900

GCAGCAAGTA TTGTTGCCGA ACAAATTGCT GGAAATGACA CTATTGAATT CAAAGGCTTC     960

TTAGGCAACA ATATTGTGAA GTTCTTTGAT TATACATTTG CGAGTGTCGG CGTTAAACCA    1020

AACGAACTAA AGCAATTTGA CTATAAAATG GTAGAAGTCA CTCAAGGTGC ACACGCGAAT    1080

TATTACCCAG GAAATTCCCC TTTACACTTA AGAGTATATT ATGACACTTC AAACCGTCAG    1140

ATTTTAAGAG CAGCTGCAGT AGGAAAAGAA GGTGCAGATA AACGTATTGA TGTACTATCG    1200
```

```
ATGGCAATGA TGAACCAGCT AACTGTAGAT GAGTTAACTG AGTTTGAAGT GGCTTATGCA      1260

CCACCATATA GCCACCCTAA AGATTTAATC AATATGATTG GTTACAAAGC TAAATAA        1317
```

(2) INFORMATION FOR SEQ ID NO:2:

(i) SEQUENCE CHARACTERISTICS:
        (A) LENGTH: 438 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:2:

```
Met Pro Lys Ile Val Val Gly Ala Val Ala Gly Gly Ala Thr Cys
 1               5                  10                  15

Ala Ser Gln Ile Arg Arg Leu Asp Lys Glu Ser Asp Ile Ile Phe
                20                  25                  30

Glu Lys Asp Arg Asp Met Ser Phe Ala Asn Cys Ala Leu Pro Tyr Val
                35                  40                  45

Ile Gly Glu Val Val Glu Asp Arg Arg Tyr Ala Leu Ala Tyr Thr Pro
     50                  55                  60

Glu Lys Phe Tyr Asp Arg Lys Gln Ile Thr Val Lys Thr Tyr His Glu
65                  70                  75                  80

Val Ile Ala Ile Asn Asp Glu Arg Gln Thr Val Ser Val Leu Asn Arg
                85                  90                  95

Lys Thr Asn Glu Gln Phe Glu Glu Ser Tyr Asp Lys Leu Ile Leu Ser
                100                 105                 110

Pro Gly Ala Ser Ala Asn Ser Leu Gly Phe Glu Ser Asp Ile Thr Phe
            115                 120                 125

Thr Leu Arg Asn Leu Glu Asp Thr Asp Ala Ile Asp Gln Phe Ile Lys
    130                 135                 140

Ala Asn Gln Val Asp Lys Val Leu Val Val Gly Ala Gly Tyr Val Ser
145                 150                 155                 160

Leu Glu Val Leu Glu Asn Leu Asn Glu Arg Gly Leu His Pro Thr Leu
                165                 170                 175

Ile Asn Arg Ser Asp Lys Ile Asn Lys Leu Met Asp Ala Asp Met Asn
                180                 185                 190

Gln Pro Ile Leu Asp Glu Leu Asp Lys Arg Glu Ile Pro Tyr Arg Leu
            195                 200                 205

Asn Glu Glu Ile Asn Ala Ile Asn Gly Asn Glu Ile Thr Phe Lys Ser
    210                 215                 220

Gly Lys Val Glu His Tyr Asp Met Ile Ile Glu Gly Val Gly Thr His
225                 230                 235                 240

Pro Asn Ser Lys Phe Ile Glu Ser Asn Ile Lys Leu Asp Arg Lys
                245                 250                 255

Gly Phe Ile Pro Val Asn Asp Lys Phe Glu Thr Asn Val Pro Asn Ile
            260                 265                 270

Tyr Ala Ile Gly Asp Ile Ala Thr Ser His Tyr Arg His Val Asp Leu
        275                 280                 285

Pro Ala Ser Val Pro Leu Ala Trp Gly Ala His Arg Ala Ala Ser Ile
    290                 295                 300

Val Ala Glu Gln Ile Ala Gly Asn Asp Thr Ile Glu Phe Lys Gly Phe
305                 310                 315                 320

Leu Gly Asn Asn Ile Val Lys Phe Phe Asp Tyr Thr Phe Ala Ser Val
```

```
                    325                 330                 335
Gly Val Lys Pro Asn Glu Leu Lys Gln Phe Asp Tyr Lys Met Val Glu
            340                 345                 350

Val Thr Gln Gly Ala His Ala Asn Tyr Tyr Pro Gly Asn Ser Pro Leu
        355                 360                 365

His Leu Arg Val Tyr Tyr Asp Thr Ser Asn Arg Gln Ile Leu Arg Ala
370                 375                 380

Ala Ala Val Gly Lys Glu Gly Ala Asp Lys Arg Ile Asp Val Leu Ser
385                 390                 395                 400

Met Ala Met Met Asn Gln Leu Thr Val Asp Glu Leu Thr Glu Phe Glu
                405                 410                 415

Val Ala Tyr Ala Pro Pro Tyr Ser His Pro Lys Asp Leu Ile Asn Met
            420                 425                 430

Ile Gly Tyr Lys Ala Lys
            435
```

(2) INFORMATION FOR SEQ ID NO:3:

(i) SEQUENCE CHARACTERISTICS:
        (A) LENGTH: 14 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:3:

```
Pro Lys Ile Val Val Val Gly Ala Val Ala Gly Gly Ala Thr
1               5                   10
```

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Other nucleic acid (ix) FEATURE: N-terminal region (xi) SEQUENCE DESCRIPTION: SEQ ID NO:4:

```
GGATGCATGT ACTGCATGGA TGGATGC                                          27
```

(2) INFORMATION FOR SEQ ID NO:5:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other nucleic acid (ix) FEATURE: internal region (xi) SEQUENCE DESCRIPTION: SEQ ID NO:5:

```
AAGATGCAAA ATAGAGTTAA TAGAGTTATA TATCCAAC                              38
```

(2) INFORMATION FOR SEQ ID NO:6:

(i) SEQUENCE CHARACTERISTICS:
        (A) LENGTH: 15 amino acids
        (B) TYPE: amino acid (C) STRANDEDNESS: single
            (D) TOPOLOGY: unknown (ii) MOLECULE TYPE: peptide (v) FRAGMENT TYPE: N-terminal fragment (xi) SEQUENCE DESCRIPTION: SEQ ID NO:6:

Pro Pro Lys Ile Val Val Val Gly Ala Val Ala Gly Gly Ala Thr
1               5                  10                  15

(2) INFORMATION FOR SEQ ID NO:7:

(i) SEQUENCE CHARACTERISTICS:
            (A) LENGTH: 16 amino acids
            (B) TYPE: amino acid
            (C) STRANDEDNESS: single
            (D) TOPOLOGY: unknown (ii) MOLECULE TYPE: peptide (v) FRAGMENT TYPE: internal fragment (xi) SEQUENCE DESCRIPTION: SEQ ID NO:7:

Asn Gln Pro Ile Leu Asp Glu Ser Asp Lys Arg Glu Ile Pro Tyr Pro
1               5                  10                  15

(2) INFORMATION FOR SEQ ID NO:8:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: Other nucleic acid (xi) SEQUENCE DESCRIPTION: SEQ ID NO:8:

GGGAATTCCA TATGCCCAAA ATAGTCGTAG TCGG                                    34

(2) INFORMATION FOR SEQ ID NO:9:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: Other nucleic acid (xi) SEQUENCE DESCRIPTION: SEQ ID NO:9:

CCCAAGCTTT ATTTAGCTTT GTAACCAATC AT                                      32

(2) INFORMATION FOR SEQ ID NO:10:

(i) SEQUENCE CHARACTERISTICS:
            (A) LENGTH: 1317 base pairs
            (B) TYPE: nucleic acid
            (C) STRANDEDNESS: double
            (D) TOPOLOGY: linear (ii) MOLECULE TYPE: Genomic DNA (xi) SEQUENCE DESCRIPTION: SEQ ID NO:10:

ATGAATAAAA TTATAATAGT CGGTGCAGTT GCTGGTGGTG CGACTTGTGC AAGTCAAATT         60

CGAAGATTAG ATAAAGAGAG TGAAATCATT GTTTTTGAAA AAGATAGAGA CATGAGCTTT        120

GCTAATTGTG CATTACCTTA TTATATTGGC AACGTTATCG AGGACCGTCG TAAAGTTTTA        180

-continued

```
GCATACACGC CCAATCAATT TTATGACAAA AAGCAAATCA CTGTAAAAAC ATACCATGAA    240

GTTATACAAA TCAATGATGA GAGACAAACA GTTACTGTCT TAAATCATCA AACTAATCAA    300

ACTTTTGAAG AAAGTTACGA TACATTGATT TTAAGTCCTG GCGCATCTGC AAATCGATTA    360

AACACTCATA GTGATATCTC ATTTACTGTG CGAAATCTCG AAGATACTGA AACAATTGAT    420

ACCTTTATTA CGAATACCAA AGCACAACGT GCACTTGTTG TTGGCGCGGG TTACATCTCT    480

TTAGAAGTCC TTGAAAATTT ACATCATAGA GGTTTGGATG TCACATGGAT TCATCGCTCT    540

ACAAATATTA ATAAACTGAT GGATCAAGAT ATGAATCAAC CCATCATCGA CGAAATAGAA    600

AAGAGAAATA TCACTTATAG ATTTAACGAA GAAATTAGTC ACGTAAATGG ACATGAAGTT    660

ACATTCACAT CTGGTAAAGT TGAAAACTTT GATCTTATTA TCGAAGGTGT AGGTACTCAT    720

CCAAATTCAC AATTTATTAA ATCATCTAAC GTCATACTGA ATGATAAAGG TTATATCCCA    780

GTAAATCATA ATTTCCAAAC AAATATACCA AATATTTATG CATTAGGTGA TGTTATTACT    840

TCACATTATC GTCATGTGAA TTTACCGGCA CAGGTTCCAC TTGCTTGGGG AGCACACCGT    900

GGTGCAAGTA TTATAGCTGA ACAACTTTCT GGAAATTCGT CTATTCACTT TAAAGGTTAT    960

CTAGGAAATA ATATAGTGAA ATTTTTTGAC TATACATTAG CAAGTGTTGG CATCAAACCA   1020

AATGAACTTA AAAATTTCGA TTATGATATG GTTGAAGTTA AGCAAGGAGC TCATGCAGGA   1080

TATTACCCAG GAAATTCACC ACTACATTTA CGTGTTTATT TTGAAAAAGA CTCGAGAAAA   1140

CTTATACGCG CAGCAGCAGT TGGTAAACAA GGTGCCGATA AAAGAATAGA CGTATTATCA   1200

ATGGCAATGA TGAATAATGC TACTGTGGAT GATTTAACAG AATTTGAAGT AGCATATGCA   1260

CCTCCTTATA GTCATCCAAA AGATTTAATT AATTTAATTG GGTATAAAGC GCAATAA     1317
```

(2) INFORMATION FOR SEQ ID NO:11:

(i) SEQUENCE CHARACTERISTICS:
        (A) LENGTH: 438 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:11:

```
Met Asn Lys Ile Ile Ile Val Gly Ala Val Ala Gly Gly Ala Thr Cys
  1               5                  10                  15

Ala Ser Gln Ile Arg Arg Leu Asp Lys Glu Ser Glu Ile Ile Val Phe
             20                  25                  30

Glu Lys Asp Arg Asp Met Ser Phe Ala Asn Cys Ala Leu Pro Tyr Tyr
         35                  40                  45

Ile Gly Asn Val Ile Glu Asp Arg Arg Lys Val Leu Ala Tyr Thr Pro
     50                  55                  60

Asn Gln Phe Tyr Asp Lys Lys Gln Ile Thr Val Lys Thr Tyr His Glu
 65                  70                  75                  80

Val Ile Gln Ile Asn Asp Glu Arg Gln Thr Val Thr Val Leu Asn His
                 85                  90                  95

Gln Thr Asn Gln Thr Phe Glu Glu Ser Tyr Asp Thr Leu Ile Leu Ser
            100                 105                 110

Pro Gly Ala Ser Ala Asn Arg Leu Asn Thr His Ser Asp Ile Ser Phe
        115                 120                 125

Thr Val Arg Asn Leu Glu Asp Thr Glu Thr Ile Asp Thr Phe Ile Thr
    130                 135                 140

Asn Thr Lys Ala Gln Arg Ala Leu Val Val Gly Ala Gly Tyr Ile Ser
```

```
145                 150                 155                 160
Leu Glu Val Leu Glu Asn Leu His His Arg Gly Leu Asp Val Thr Trp
                165                 170                 175
Ile His Arg Ser Thr Asn Ile Asn Lys Leu Met Asp Gln Asp Met Asn
                180                 185                 190
Gln Pro Ile Ile Asp Glu Ile Glu Lys Arg Asn Ile Thr Tyr Arg Phe
                195                 200                 205
Asn Glu Glu Ile Ser His Val Asn Gly His Glu Val Thr Phe Thr Ser
            210                 215                 220
Gly Lys Val Glu Asn Phe Asp Leu Ile Ile Glu Gly Val Gly Thr His
225                 230                 235                 240
Pro Asn Ser Gln Phe Ile Lys Ser Ser Asn Val Ile Leu Asn Asp Lys
                245                 250                 255
Gly Tyr Ile Pro Val Asn His Asn Phe Gln Thr Asn Ile Pro Asn Ile
                260                 265                 270
Tyr Ala Leu Gly Asp Val Ile Thr Ser His Tyr Arg His Val Asn Leu
            275                 280                 285
Pro Ala Gln Val Pro Leu Ala Trp Gly Ala His Arg Gly Ala Ser Ile
            290                 295                 300
Ile Ala Glu Gln Leu Ser Gly Asn Ser Ser Ile His Phe Lys Gly Tyr
305                 310                 315                 320
Leu Gly Asn Asn Ile Val Lys Phe Phe Asp Tyr Thr Leu Ala Ser Val
                325                 330                 335
Gly Ile Lys Pro Asn Glu Leu Lys Asn Phe Asp Tyr Asp Met Val Glu
            340                 345                 350
Val Lys Gln Gly Ala His Ala Gly Tyr Tyr Pro Gly Asn Ser Pro Leu
            355                 360                 365
His Leu Arg Val Tyr Phe Glu Lys Asp Ser Arg Lys Leu Ile Arg Ala
        370                 375                 380
Ala Ala Val Gly Lys Gln Gly Ala Asp Lys Arg Ile Asp Val Leu Ser
385                 390                 395                 400
Met Ala Met Met Asn Asn Ala Thr Val Asp Asp Leu Thr Glu Phe Glu
                405                 410                 415
Val Ala Tyr Ala Pro Pro Tyr Ser His Pro Lys Asp Leu Ile Asn Leu
            420                 425                 430
Ile Gly Tyr Lys Ala Gln
        435
```

(2) INFORMATION FOR SEQ ID NO:12:

(i) SEQUENCE CHARACTERISTICS:
        (A) LENGTH: 1650 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:12:

```
ATGAAAATTG TAATTATCGG AGGCGTGGCT GGTGGTATGT CAGCAGCGAC ACGTTTACGT      60

CGTTTAATGG AAGATGCTGA AATTGTTGTC ATGGAAAAAG GCCCTTTTGT TTCATTTGCA     120

AACTGTGGTT TGACTTACTA CGTTTCTGGC GAAATCGCAG AAAGAGAGCA ACTGCTTGTT     180

CAAACACCCG AAGCGTTAAA GGCACGGTTT AATTTAGATG TTCGTCCTCA CCATGAAGTC     240

GTGGCGATTG ATCCAATAGA AAAAGTGATC ACAGTGAAAC ATGAAACAGA AATTTTAACA     300
```

-continued

```
GAACACTATG ACAAATTAAT TTTATCACCA GGGGCGAAAC CTTTTGTGCC ACCAATTACA      360

GGATTGGCAG AAGCCAAAAA TGTTTTTTCA TTAAGAAATG TTCCTGATTT AGATCAAATT      420

ATGACAGCCT TGACACCAGA AACAAAACGA GCCGTCGTGA TTGGCGCAGG CTTCATTGGC      480

TTGGAAATGG CAGAAAACTT GCAAAACGC GGATTAGAAG TCACTCTCGT GGAAAAAGCG      540

CCTCATGTTT TACCGCCATT AGACGAAGAA ATGGCCGCTT TTGTCAAAGC TGAATTAAGC      600

AAAAACAATG TTCAAGTAAT TACGGGACAA TCTGCGGTTG CTTTTGAAGA AGAAGGGCAA      660

GTGATTCGCT TAGAAGACGG TCAAACATTA GCTTCTGATT TAACCATTTT GTCGGTGGGT      720

GTCCAACCAG AAAATACCTT AGCAGTTGAA GCAGGTGTAG CAACTGGTTT ACGTGGCGGT      780

ATTGTTGTTG ATGAACACTA TCAAACGAAT CAACCCGATA TTTATGCGGT TGGGGATGCT      840

GTTGTAGTGA ACAACAAAT CACTCAAGAA GATGCGCTGA TTTCTTTAGC TTCTCCTGCC      900

AATCGCCAAG GACGTCAAGT AGCGGATGTG ATTGCTGGGT TAGAGAGAAA AAATCAAGGA      960

AGCATTGGGA CTGCCATTGT GCGAGTCTTT GATTTAACCG CTGCTTCAAC TGGTTTAAGC     1020

GAACGGGCTG CTAAAGCTGC TGGACTAACA ACAGCTGTTG TGCATATCAG TGGAAAAGAC     1080

CATGCGGGGT ATTATCCTGG CGCAACAGAT CTTCAGTTAA AATTAGTTTT TCATCCTACG     1140

ACAGGGGAAA TTTATGGCGC ACAAGGAATT GGGGCAAAGG GCGTAGATAA GCGGATTGAT     1200

ATTCTTGCGA CCGCTATTAA AGGACAGTTA ACTATTTTTG ATTTGCCTGA ATTAGAGTTT     1260

ACCTATGCGC CGCCGTTTGG TTCAGCGAAA GATCCTGTGA ACATGTTAGG CTATGCAGCG     1320

ATGAACCTTG CAGAAGGATT GAGTGAAAAC ATTCAATGGT ATGAGCTATC CAACGAATTA     1380

GCTAATGGGG CTGTTTTATT AGATGTCCGT AATCCCGCCG AACGAGCCAA TGGTCAATTT     1440

AAAAATGCTG TGTCTATTCC TTTAAATGAG TTAAGAGAAC GTTGGAGGA ATTAGACAAG     1500

TCAACGGAGT ACATTGTTAG TTGTCACAGC GGTTTGCGTA GTTATATTGC AGAACGGATG     1560

CTAAAACAAG CGGGCATCTC AGCCAAAAAT TTAGATGGTG CTTTTGCGCT ATATCGAATG     1620

GTAAAATCGG AGGAACTAGA AAATGTATAA                                    1650
```

(2) INFORMATION FOR SEQ ID NO:13:

(i) SEQUENCE CHARACTERISTICS:
        (A) LENGTH: 549 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:13:

```
Met Lys Ile Val Ile Gly Gly Val Ala Gly Met Ser Ala Ala
 1               5                  10                  15

Thr Arg Leu Arg Arg Leu Met Glu Asp Ala Glu Ile Val Met Glu
                20                  25                  30

Lys Gly Pro Phe Val Ser Phe Ala Asn Cys Gly Leu Thr Tyr Tyr Val
         35                  40                  45

Ser Gly Glu Ile Ala Glu Arg Glu Gln Leu Leu Val Gln Thr Pro Glu
         50                  55                  60

Ala Leu Lys Ala Arg Phe Asn Leu Asp Val Arg Pro His His Glu Val
65                   70                  75                  80

Val Ala Ile Asp Pro Ile Glu Lys Val Ile Thr Val Lys His Glu Thr
                     85                  90                  95

Glu Ile Leu Thr Glu His Tyr Asp Lys Leu Ile Leu Ser Pro Gly Ala
                100                 105                 110
```

-continued

```
Lys Pro Phe Val Pro Pro Ile Thr Gly Leu Ala Glu Ala Lys Asn Val
            115                 120                 125
Phe Ser Leu Arg Asn Val Pro Asp Leu Asp Gln Ile Met Thr Ala Leu
        130                 135                 140
Thr Pro Glu Thr Lys Arg Ala Val Val Ile Gly Ala Gly Phe Ile Gly
145                 150                 155                 160
Leu Glu Met Ala Glu Asn Leu Gln Lys Arg Gly Leu Glu Val Thr Leu
                165                 170                 175
Val Glu Lys Ala Pro His Val Leu Pro Pro Leu Asp Glu Glu Met Ala
            180                 185                 190
Ala Phe Val Lys Ala Glu Leu Ser Lys Asn Asn Val Gln Val Ile Thr
        195                 200                 205
Gly Gln Ser Ala Val Ala Phe Glu Glu Gly Gln Val Ile Arg Leu
    210                 215                 220
Glu Asp Gly Gln Thr Leu Ala Ser Asp Leu Thr Ile Leu Ser Val Gly
225                 230                 235                 240
Val Gln Pro Glu Asn Thr Leu Ala Val Glu Ala Gly Val Ala Thr Gly
                245                 250                 255
Leu Arg Gly Gly Ile Val Val Asp Glu His Tyr Gln Thr Asn Gln Pro
            260                 265                 270
Asp Ile Tyr Ala Val Gly Asp Ala Val Val Lys Gln Gln Ile Thr
        275                 280                 285
Gln Glu Asp Ala Leu Ile Ser Leu Ala Ser Pro Ala Asn Arg Gln Gly
    290                 295                 300
Arg Gln Val Ala Asp Val Ile Ala Gly Leu Glu Arg Lys Asn Gln Gly
305                 310                 315                 320
Ser Ile Gly Thr Ala Ile Val Arg Val Phe Asp Leu Thr Ala Ala Ser
                325                 330                 335
Thr Gly Leu Ser Glu Arg Ala Ala Lys Ala Ala Gly Leu Thr Thr Ala
            340                 345                 350
Val Val His Ile Ser Gly Lys Asp His Ala Gly Tyr Tyr Pro Gly Ala
        355                 360                 365
Thr Asp Leu Gln Leu Lys Leu Val Phe His Pro Thr Thr Gly Glu Ile
    370                 375                 380
Tyr Gly Ala Gln Gly Ile Gly Ala Lys Gly Val Asp Lys Arg Ile Asp
385                 390                 395                 400
Ile Leu Ala Thr Ala Ile Lys Gly Gln Leu Thr Ile Phe Asp Leu Pro
                405                 410                 415
Glu Leu Glu Phe Thr Tyr Ala Pro Pro Phe Gly Ser Ala Lys Asp Pro
            420                 425                 430
Val Asn Met Leu Gly Tyr Ala Ala Met Asn Leu Ala Glu Gly Leu Ser
        435                 440                 445
Glu Asn Ile Gln Trp Tyr Glu Leu Ser Asn Glu Leu Ala Asn Gly Ala
    450                 455                 460
Val Leu Leu Asp Val Arg Asn Pro Ala Glu Arg Ala Asn Gly Gln Phe
465                 470                 475                 480
Lys Asn Ala Val Ser Ile Pro Leu Asn Glu Leu Arg Glu Arg Leu Glu
                485                 490                 495
Glu Leu Asp Lys Ser Thr Glu Tyr Ile Val Ser Cys His Ser Gly Leu
            500                 505                 510
Arg Ser Tyr Ile Ala Glu Arg Met Leu Lys Gln Ala Gly Ile Ser Ala
        515                 520                 525
```

Lys Asn Leu Asp Gly Ala Phe Ala Leu Tyr Arg Met Val Lys Ser Glu
    530                 535                 540

Glu Leu Glu Asn Val
545

(2) INFORMATION FOR SEQ ID NO:14:

(i) SEQUENCE CHARACTERISTICS:
        (A) LENGTH: 1656 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:14:

```
ATGAAAATCG TTATTGTCGG AGGTGTAGCA GGTGGAATGT CTGCTGCTAC ACGGCTTCGC      60
CGATTAATGG AAGATGCAGA AATCGTTGTT TTTGAAAAAG ACCGTATGT TTCTTTTGCA     120
AATTGCGGCT TGCCTTATTA TCTTTCGGGA GAAATCAGTG AACGGGAAAA TCTTCTTGTC    180
CAAACGCCAG AATCATTATC CGCTCGTTTT TGTTTAGATG TGCGTCCAAA TCATGAAGTG    240
ACAGCCATCT TTCCCGAAAA CAAAACGGTA GAAGTCGTAC ATGAGGGTCA AAAACACATT    300
GAACAGTACG ATGCATTGGT TTTATCTCCT GGTGCAAAAC CAGTTGTTCC ATCGATTCCA    360
GGGATAACAG AAGCCGACAA TGTTTTTTCT ATTAGAAATG TACCAGATAT CGATAAAGTG    420
ATACATGCAT TAGAAAAACA GCCAAAGCGT GCCGTGATCG TTGGTGCAGG ATTCATCGGA    480
TTGGAAATGG CAGAAAACCT AAAAAGAAGA GGTTTAGAAG TCATGGTGAT CGAACAAGCA    540
CCACATATTC TTCCGACGCT GGATGAAGAA ATGGCAGCTT TTATAGAAAA AGAATTGTCT    600
CATCAAGGAG TAGAAGTGAT TACTTCTCAT GCTGTCGCTG GATTTGAAGA CCACGGGAAA    660
CGATTGCGAC TGGATGATGG GCGTACCATC CCTGCTGATT TAGTTATTTT ATCCATTGGT    720
GTTCGTCCTG ATAACCAGCT AGCAGTGACT GCTGGAATCG AATTAGGTAT ACGCGGGGGT    780
ATCCTAGTAG ACGAACGATA TCAAACGAAT ATTCCTGATA TTTATGCGGT GGGGGATGCT    840
ATCGTTGTAA ACAGCAAAT CACTGGAAAA GATGCACTTA TTTCTCTTGC TTCACCAGCC     900
AATCGTCAAG GTAGACAAGT TGCGGACACG ATTTCCGGAA TTTCTCGAAG AAATCAAGGC    960
GGTATTGGAA CAGCAATTAT ACGAACGTTT GGAATGACTG CCGCATCCAC CGGTTTAAGT   1020
GAAAGAACAG CCAAAGAAAA CGAACTGTCT TTTGAAGTCA TTCATGTATC AGGAAAAGAT   1080
CATGCAAGCT ATTATCCAGA AGCAACAGAT ATTTTACTGA AGTTGATCTT CCATCCAGAG   1140
ACTGGCGAGA TTTATGGTGC ACAAGGTGTT GGGGCAAAAG GTGTGGATAA ACGGATCGAT   1200
ATTTTAGCAA CAGCAATCAA AGGGCATTTG ACGATCTTCG ATTTACCGGA ATTAGAATTG   1260
ACGTATGCAC CGCCATTTGG CTCAGCCAAA GATCCAGTAA ACATGCTAGG ATATGCAGCA   1320
ATGAACATTG TAGAAGGGCT TAGTGAAACC GTACAATGGC ATGAATTGCC GACAGAATTA   1380
GCAAAAGGAA AAATTTTATT AGATGTGCGA ACAGCAGAAG AATTGGAAAA AGGCAAATTC   1440
AAGGAAGCCA AACATATCCC TTTGAATGAA CTTCGAGACC GATTAGATGA ATTAGACAGC   1500
CAGCAAGAAT ATATCGTCAG CTGTCATAGT GGGCTACGTA GCTATCTAGC GGAAAGAATC   1560
TTGAAGCAGT CTGGCTACCA CGTAAAAAAC CTTGATGGTG CATTTTCTTT ATATCAAACT   1620
GTCCGACAAG AAGAACTGAT ATATCCTAAC AAATGA                             1656
```

(2) INFORMATION FOR SEQ ID NO:15:

(i) SEQUENCE CHARACTERISTICS:

-continued (A) LENGTH: 551 amino acids
  (B) TYPE: amino acid
  (C) STRANDEDNESS: single
  (D) TOPOLOGY: unknown (ii) MOLECULE TYPE: protein (xi) SEQUENCE DESCRIPTION: SEQ ID NO:15:

Met Lys Ile Val Ile Val Gly Gly Val Ala Gly Met Ser Ala Ala
 1               5                  10                  15

Thr Arg Leu Arg Arg Leu Met Glu Asp Ala Glu Ile Val Val Phe Glu
             20                  25                  30

Lys Gly Pro Tyr Val Ser Phe Ala Asn Cys Gly Leu Pro Tyr Tyr Leu
             35                  40                  45

Ser Gly Glu Ile Ser Glu Arg Glu Asn Leu Leu Val Gln Thr Pro Glu
 50                  55                  60

Ser Leu Ser Ala Arg Phe Cys Leu Asp Val Arg Pro Asn His Glu Val
 65                  70                  75                  80

Thr Ala Ile Phe Pro Glu Asn Lys Thr Val Glu Val His Glu Gly
             85                  90                  95

Gln Lys His Ile Glu Gln Tyr Asp Ala Leu Val Leu Ser Pro Gly Ala
             100                 105                 110

Lys Pro Val Val Pro Ser Ile Pro Gly Ile Thr Glu Ala Asp Asn Val
             115                 120                 125

Phe Ser Ile Arg Asn Val Pro Asp Ile Asp Lys Val Ile His Ala Leu
130                 135                 140

Glu Lys Gln Pro Lys Arg Ala Val Ile Val Gly Ala Gly Phe Ile Gly
145                 150                 155                 160

Leu Glu Met Ala Glu Asn Leu Lys Arg Arg Gly Leu Glu Val Met Val
             165                 170                 175

Ile Glu Gln Ala Pro His Ile Leu Pro Thr Leu Asp Glu Glu Met Ala
             180                 185                 190

Ala Phe Ile Glu Lys Glu Leu Ser His Gln Gly Val Glu Val Ile Thr
             195                 200                 205

Ser His Ala Val Ala Gly Phe Glu Asp His Gly Lys Arg Leu Arg Leu
             210                 215                 220

Asp Asp Gly Arg Thr Ile Pro Ala Asp Leu Val Ile Leu Ser Ile Gly
225                 230                 235                 240

Val Arg Pro Asp Asn Gln Leu Ala Val Thr Ala Gly Ile Glu Leu Gly
             245                 250                 255

Ile Arg Gly Gly Ile Leu Val Asp Glu Arg Tyr Gln Thr Asn Ile Pro
             260                 265                 270

Asp Ile Tyr Ala Val Gly Asp Ala Ile Val Val Lys Gln Gln Ile Thr
             275                 280                 285

Gly Lys Asp Ala Leu Ile Ser Leu Ala Ser Pro Ala Asn Arg Gln Gly
             290                 295                 300

Arg Gln Val Ala Asp Thr Ile Ser Gly Ile Ser Arg Arg Asn Gln Gly
305                 310                 315                 320

Gly Ile Gly Thr Ala Ile Ile Arg Thr Phe Gly Met Thr Ala Ala Ser
             325                 330                 335

Thr Gly Leu Ser Glu Arg Thr Ala Lys Glu Asn Glu Leu Ser Phe Glu
             340                 345                 350

Val Ile His Val Ser Gly Lys Asp His Ala Ser Tyr Tyr Pro Glu Ala
             355                 360                 365

Thr Asp Ile Leu Leu Lys Leu Ile Phe His Pro Glu Thr Gly Glu Ile

```
          370                375                380
Tyr Gly Ala Gln Gly Val Gly Ala Lys Gly Val Asp Lys Arg Ile Asp
385                 390                 395                 400

Ile Leu Ala Thr Ala Ile Lys Gly His Leu Thr Ile Phe Asp Leu Pro
                405                 410                 415

Glu Leu Glu Leu Thr Tyr Ala Pro Pro Phe Gly Ser Ala Lys Asp Pro
                420                 425                 430

Val Asn Met Leu Gly Tyr Ala Ala Met Asn Ile Val Glu Gly Leu Ser
            435                 440                 445

Glu Thr Val Gln Trp His Glu Leu Pro Thr Glu Leu Ala Lys Gly Lys
        450                 455                 460

Ile Leu Leu Asp Val Arg Thr Ala Glu Glu Leu Glu Lys Gly Lys Phe
465                 470                 475                 480

Lys Glu Ala Lys His Ile Pro Leu Asn Glu Leu Arg Asp Arg Leu Asp
                485                 490                 495

Glu Leu Asp Ser Gln Gln Glu Tyr Ile Val Ser Cys His Ser Gly Leu
                500                 505                 510

Arg Ser Tyr Leu Ala Glu Arg Ile Leu Lys Gln Ser Gly Tyr His Val
            515                 520                 525

Lys Asn Leu Asp Gly Ala Phe Ser Leu Tyr Gln Thr Val Arg Gln Glu
        530                 535                 540

Glu Leu Ile Tyr Pro Asn Lys
545                 550

(2) INFORMATION FOR SEQ ID NO:16:

(i) SEQUENCE CHARACTERISTICS:
        (A) LENGTH: 1614 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:16:

ATGAAAGTTG TTGTCATTGG CGGTGTAGCT GGCGGTCCTT CATTTGCCAC TCGTTTCCGT    60

CGATTGAATG AAGCACACGA AATCATTATC TATGAACGCG GAGAGAATAT TTCTTACGCA   120

AGTTGTGCTT TGCCTTATTA TTTAGGTGGT GTGATCACGG ACCGTGACTC GCTGATCGAA   180

CGTACACCAG AAATATTGAA AACAAAAAAC AACATCGACG TATTTACTAA ACACGAAGTA   240

ACAGCAATCG ATCCTTCTAC TAAGCGATTA ACAGTTAAAG ACCTATCCAC AAATGAAGAA   300

ACAAAAACAG ATTACGATAA GTTGATCATC TCTTCTGGTG CTAGACCAGA TTATCCGGAT   360

ATTCCCGGAG TTTTTGAAGC AGAAAACGGC TTTGTACTCC GTAGTGTGAC GGATGCGGAT   420

CGAATCAAAT CGTTCCTTGA AGAAAAAAAT CCACAACATG TCGTCATTCT TGGTGCAGGT   480

GTTATGGGTC TGGAATTAGC TGAGAATCTC AAGCATCGCG GCTTAAACGT GACTTTAATC   540

GATCAATTGC CACAAGTCGC TTTCCCTTAT GATCCAGAAA TTGCTAATTT AGTTTATGAC   600

AAATTGCTGA AGAAGGATT AGCCGTTCAT TTAGAAACAA GAGTTACTGA GATCCGTGAT   660

AAAGGTCGAG AAATAATATT ATCAGATGGT TCCGTCCTTT CTGCTGATAT GCTAATTTTT   720

GCTGTTGGTG TTTCTCCGAA TAATGAAGTG GTGAAAGCAG CCGGCATAAA ATTATCTGAT   780

ACAGGACAGA TCATTGTCGA TGACCAGTTA CAAACCAATC TTCCGGACAT CTATGCGATT   840

GGCGATATTA TCGAAACAAC TAGTGTAGTG ACTGGTCAGC CGATCCAAAG TATGCTTTCC   900

AGTGCGGCCA ATCGTCAAGG ACACATGTTG GCAGATATTT TAAATGGTAC GCCTATGCGC   960
```

-continued

```
TATCGCGGAT ATATTGGTGC AGGTGTCGCA AAAATCTTTG ATCATACAGC AAGTTATGCT      1020

GGAATGACAG AACATGCACT AAAAGCATCA GGCATAACAA ATTATAAAAC TGTTTTTATC      1080

ACTCCTTTTG ACCATGCCTA TTTCTATCCA GGAGCTACAA GATTAAATCT AAAGCTGATT      1140

TTTGATGCAG ATAGCGGTCG TATTTTAGGT GGACAAGCAT TTGGAGAAAA AGGTGTCGAT      1200

AAACGGATGG GAGAACTTTC TGTAGCGATC ACCGGAAACT TGACAGTCTT TGATTTGCCC      1260

GATTTGGAGT TGCCTTACTC TCCACCGTAT TCTACTACCC GTGATCCGTT GAATATAGCT      1320

GGTTATGTCG CAATCAATCA AATGACGAAT ATCGTAGAAA CGATCAAAGC AAGTGATATA      1380

CCCGAAAACG ATTTGAAAGA AGCGTTCTTT TTAGACATAC GTGAACCTAA TAAAGCACCT      1440

CCCGAAAACG ATTTGAAAGA AGCGTTCTTT TTAGACATAC GTGAACCTAA TAAAGCACCT      1500

GAAATCCCAA AAGATAAAAA AATTTATATT ACTTTCAGAA GAGGATTGAA TACTTATACT      1560

TCTGCCCGAA TCTTGGCAGG TTTGGGTATC AAAGCGGTTT TGATTGAAGA ATAA           1614
```

(2) INFORMATION FOR SEQ ID NO:17:

(i) SEQUENCE CHARACTERISTICS:
        (A) LENGTH: 537 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:17:

```
Met Lys Val Val Ile Gly Gly Val Ala Gly Gly Pro Ser Phe Ala
 1               5                  10                  15

Thr Arg Phe Arg Arg Leu Asn Glu Ala His Glu Ile Ile Tyr Glu
                20                  25                  30

Arg Gly Glu Asn Ile Ser Tyr Ala Ser Cys Ala Leu Pro Tyr Tyr Leu
            35                  40                  45

Gly Gly Val Ile Thr Asp Arg Asp Ser Leu Ile Glu Arg Thr Pro Glu
        50                  55                  60

Ile Leu Lys Thr Lys Asn Asn Ile Asp Val Phe Thr Lys His Glu Val
65                  70                  75                  80

Thr Ala Ile Asp Pro Ser Thr Lys Arg Leu Thr Val Lys Asp Leu Ser
                85                  90                  95

Thr Asn Glu Glu Thr Lys Thr Asp Tyr Asp Lys Leu Ile Ile Ser Ser
                100                 105                 110

Gly Ala Arg Pro Asp Tyr Pro Asp Ile Pro Gly Val Phe Glu Ala Glu
            115                 120                 125

Asn Gly Phe Val Leu Arg Ser Val Thr Asp Ala Asp Arg Ile Lys Ser
    130                 135                 140

Phe Leu Glu Glu Lys Asn Pro Gln His Val Val Ile Leu Gly Ala Gly
145                 150                 155                 160

Val Met Gly Leu Glu Leu Ala Glu Asn Leu Lys His Arg Gly Leu Asn
                165                 170                 175

Val Thr Leu Ile Asp Gln Leu Pro Gln Val Ala Phe Pro Tyr Asp Pro
            180                 185                 190

Glu Ile Ala Asn Leu Val Tyr Asp Lys Leu Leu Lys Glu Gly Leu Ala
        195                 200                 205

Val His Leu Glu Thr Arg Val Thr Glu Ile Arg Asp Lys Gly Arg Glu
    210                 215                 220

Ile Ile Leu Ser Asp Gly Ser Val Leu Ser Ala Asp Met Leu Ile Phe
```

```
               225                 230                 235                 240
    Ala Val Gly Val Ser Pro Asn Asn Glu Val Val Lys Ala Ala Gly Ile
                    245                 250                 255
    Lys Leu Ser Asp Thr Gly Gln Ile Ile Val Asp Asp Gln Leu Gln Thr
                    260                 265                 270
    Asn Leu Pro Asp Ile Tyr Ala Ile Gly Asp Ile Ile Glu Thr Thr Ser
                    275                 280                 285
    Val Val Thr Gly Gln Pro Ile Gln Ser Met Leu Ser Ala Ala Asn
        290                 295                 300
    Arg Gln Gly His Met Leu Ala Asp Ile Leu Asn Gly Thr Pro Met Arg
    305                 310                 315                 320
    Tyr Arg Gly Tyr Ile Gly Ala Gly Val Ala Lys Ile Phe Asp His Thr
                    325                 330                 335
    Ala Ser Tyr Ala Gly Met Thr Glu His Ala Leu Lys Ala Ser Gly Ile
                    340                 345                 350
    Thr Asn Tyr Lys Thr Val Phe Ile Thr Pro Phe Asp His Ala Tyr Phe
                    355                 360                 365
    Tyr Pro Gly Ala Thr Arg Leu Asn Leu Lys Leu Ile Phe Asp Ala Asp
        370                 375                 380
    Ser Gly Arg Ile Leu Gly Gly Gln Ala Phe Gly Glu Lys Gly Val Asp
    385                 390                 395                 400
    Lys Arg Met Gly Glu Leu Ser Val Ala Ile Thr Gly Asn Leu Thr Val
                    405                 410                 415
    Phe Asp Leu Pro Asp Leu Glu Leu Pro Tyr Ser Pro Tyr Ser Thr
                    420                 425                 430
    Thr Arg Asp Pro Leu Asn Ile Ala Gly Tyr Val Ala Ile Asn Gln Met
                    435                 440                 445
    Thr Asn Ile Val Glu Thr Ile Lys Ala Ser Asp Ile Pro Glu Asn Asp
        450                 455                 460
    Leu Lys Glu Ala Phe Phe Leu Asp Ile Arg Glu Pro Asn Lys Ala Pro
    465                 470                 475                 480
    Ser Gly Ser Ile Ser Ala Thr Lys Asn Ile Pro Met Asn Glu Leu Arg
                    485                 490                 495
    Asp Arg Ile Asn Glu Ile Pro Lys Asp Lys Lys Ile Tyr Ile Thr Phe
                    500                 505                 510
    Arg Arg Gly Leu Asn Thr Tyr Thr Ser Ala Arg Ile Leu Ala Gly Leu
                    515                 520                 525
    Gly Ile Lys Ala Val Leu Ile Glu Glu
        530                 535

(2) INFORMATION FOR SEQ ID NO:18:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (ix) FEATURE: Xaa at residue position number 2 is either Ala or Gly (xi) SEQUENCE DESCRIPTION: SEQ ID NO:18:

Gly Xaa Val Ala Gly Gly
  1               5

(2) INFORMATION FOR SEQ ID NO:19:
```

```
    (i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (ix) FEATURE: Xaa at residue position number 6 is either Ser or
        Gly.  All other Xaa residues are any L-amino acid.

(xi) SEQUENCE DESCRIPTION: SEQ ID NO:19:

Gly Xaa Gly Xaa Xaa Xaa
 1            5

(2) INFORMATION FOR SEQ ID NO:20:

(i) SEQUENCE CHARACTERISTICS:
        (A) LENGTH: 5 amino acids
        (B) TYPE: amino acid
        (C) STRANDEDNESS: single
        (D) TOPOLOGY: unknown (ii) MOLECULE TYPE: peptide (ix) FEATURE:  Xaa at residue position number 2 is either Phe
        or Tyr.  All other Xaa residues are any L-amino
        acid and preferably Ala.

(xi) SEQUENCE DESCRIPTION: SEQ ID NO:20:

Ser Xaa Xaa Xaa Cys
 1            5

(2) INFORMATION FOR SEQ ID NO:21:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: Other nucleic acid (ix) FEATURE: N-terminal primer (xi) SEQUENCE DESCRIPTION: SEQ ID NO:21:

GGCCCTCTAG AAATAATTTT GTTTAACTTT AAGAAGGAGA TATACATATG AATAAAATTA      60

TAATAGTCGG TG                                                         72

(2) INFORMATION FOR SEQ ID NO:22:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other nucleic acid (ix) FEATURE: C-terminal reverse primer (xi) SEQUENCE DESCRIPTION: SEQ ID NO:22:

CCCAAGCTTT ATTGCGCTTT ATACCCAATT AA                                   32

(2) INFORMATION FOR SEQ ID NO:23:

(i) SEQUENCE CHARACTERISTICS:
        (A) LENGTH: 34 base pairs
        (B) TYPE: nucleic acid
```

```
        (C) STRANDEDNESS: single
        (D) TOPOLOGY: linear (ii) MOLECULE TYPE: Other nucleic acid (ix) FEATURE: N-terminal primer (xi) SEQUENCE DESCRIPTION: SEQ ID NO:23:

GGGAATTCCA TATGAAAATT GTAATTATCG GAGG                              34

(2) INFORMATION FOR SEQ ID NO:24:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other nucleic acid (ix) FEATURE: C-terminal reverse primer (xi) SEQUENCE DESCRIPTION: SEQ ID NO:24:

CCCAAGCTTT TATACATTTT CTAGTTCCTC CG                                32

(2) INFORMATION FOR SEQ ID NO:25:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other nucleic acid (ix) FEATURE: N-terminal primer (xi) SEQUENCE DESCRIPTION: SEQ ID NO:25:

GGGAATTCCA TATGAAAATC GTTATTGTCG G                                 31

(2) INFORMATION FOR SEQ ID NO:26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other nucleic acid (ix) FEATURE: C-terminal reverse primer (xi) SEQUENCE DESCRIPTION: SEQ ID NO:26:

CCCAAGCTTT CATTTGTTAG GATATATCAG                                   30

(2) INFORMATION FOR SEQ ID NO:27:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other nucleic acid (ix) FEATURE: N-terminal primer (xi) SEQUENCE DESCRIPTION: SEQ ID NO:27:

GGGAATTCCA TATGAAAGTT GTTGTCATTG G                                 31
```

-continued (2) INFORMATION FOR SEQ ID NO:28:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other nucleic acid (ix) FEATURE: C-terminal reverse primer (xi) SEQUENCE DESCRIPTION: SEQ ID NO:28:

CCCAAGCTTT TATTCTTCAA TCAAAACCG                        29

(2) INFORMATION FOR SEQ ID NO:29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:29:

GGGAATTCGA TTATGACAAA AAGCAAATCA                       30

(2) INFORMATION FOR SEQ ID NO:30:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:30:

GGTTCGAATA ACGGTGTGCT CCCCAAGCAA                       30

(2) INFORMATION FOR SEQ ID NO:31:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:31:

GACCGGATCC GTTTAATTTA GATGTTCG                          28

(2) INFORMATION FOR SEQ ID NO:32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:32:

GACCGGATCC GCGATTGGCA GGAG                               24

(2) INFORMATION FOR SEQ ID NO:33:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:33:

GACCGGATCC CAAACGCCAG AATCATTATT CG                                    32

(2) INFORMATION FOR SEQ ID NO:34:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:34:

GACCGGATCC GGCTGGTGAA GCAAGAG                                          27

(2) INFORMATION FOR SEQ ID NO:35:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:35:

GAGGGAATTC AGTTGTGCTT TGCCTTATTA TTTAG                                 35

(2) INFORMATION FOR SEQ ID NO:36:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:36:

GAGGGAATTC GGAAAGCATA CTTTGG                                           26

(2) INFORMATION FOR SEQ ID NO:37:

(i) SEQUENCE CHARACTERISTICS:
        (A) LENGTH: 4 amino acids
        (B) TYPE: amino acid
        (C) STRANDEDNESS: single
        (D) TOPOLOGY: unknown (ii) MOLECULE TYPE: peptide (ix) FEATURE:  Xaa at residue position number 3 is either Asn or Ser (xi) SEQUENCE DESCRIPTION: SEQ ID NO:37:

Phe Ala Xaa C ys
  1

(2) INFORMATION FOR SEQ ID NO:38:

-continued

```
    (i) SEQUENCE CHARACTERISTICS:
        (A) LENGTH: 4 amino acids
        (B) TYPE: amino acid
        (C) STRANDEDNESS: single
        (D) TOPOLOGY: unknown (ii) MOLECULE TYPE: peptide (ix) FEATURE:   Xaa at residue position number 2 is either Ala or Ser (xi) SEQUENCE DESCRIPTION: SEQ ID NO:38:

Tyr Xaa Pro P ro
  1

(2) INFORMATION FOR SEQ ID NO:39:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:39:

Thr Thr Tyr Gly Ala Asn Ala Ala Tyr Gly T yr
  1               5                  10

(2) INFORMATION FOR SEQ ID NO:40:

(i) SEQUENCE CHARACTERISTICS:
        (A) LENGTH: 13 amino acids
        (B) TYPE: amino acid
        (C) STRANDEDNESS: single
        (D) TOPOLOGY: unknown (ii) MOLECULE TYPE: Peptide (xi) SEQUENCE DESCRIPTION: SEQ ID NO:40:

Ala Asn Gly Gly Asn Gly Gly Asn Gly Cys Arg Thr A la
  1               5                  10
```

We claim:

1. An isolated polynucleotide encoding a polypeptide comprising SEQ ID NO:18, SEQ ID NO:19 and SEQ ID NO:20 and having at least 50% overall identity to SEQ ID NO:1, wherein said polypeptide is a Coenzyme A disulfide reductase (CoADR).

2. An isolated polynucleotide encoding the CoADR of claim 1 from a Gram-positive coccus.

3. An isolated polynucleotide encoding the CoADR of claim 2 wherein the Gram-positive coccus is a staphylococcus or an enterococcus.

4. An isolated polynucleotide encoding the CoADR of claim 3 wherein the Gram-positive coccus is a staphylococcus and the staphylococcus is S. aureus or S. epidermis.

5. An isolated polynucleotide encoding the CoADR of claim 3 wherein the Gram-positive coccus is an enterococcus and the enterococcus is E. faecalis or E. faecium.

6. An isolated polynucleotide selected from the group consisting of SEQ ID NO:1, SEQ ID NO:10, SEQ ID NO:12, SEQ ID NO:14 and SEQ ID NO:16.

7. An expression vector comprising the polynucleotide of claim 1 operably linked to control sequences that direct the transcription of the polynucleotide whereby said polynucleotide is expressed in a host cell.

8. An expression vector comprising the polynucleotide of claim 2 operably linked to control sequences that direct the transcription of the polynucleotide whereby said polynucleotide is expressed in a host cell.

9. An expression vector comprising the polynucleotide of claim 3 operably linked to control sequences that direct the transcription of the polynucleotide whereby said polynucleotide is expressed in a host cell.

10. An expression vector comprising the polynucleotide of claim 4 operably linked to control sequences that direct the transcription of the polynucleotide whereby said polynucleotide is expressed in a host cell.

11. An expression vector comprising the polynucleotide of claim 5 operably linked to control sequences that direct the transcription of the polynucleotide whereby said polynucleotide is expressed in a host cell.

12. An expression vector comprising the polynucleotide of claim 6 operably linked to control sequences that direct the transcription of the polynucleotide whereby said polynucleotide is expressed in a host cell.

13. A host cell comprising the expression vector of claim 7.

14. A host cell comprising the expression vector of claim 8.

15. A host cell comprising the expression vector of claim 9.

16. A host cell comprising the expression vector of claim 10.

17. A host cell comprising the expression vector of claim 11.

18. A host cell comprising the expression vector of claim 12.

19. A method for producing a Coenzyme A disulfide reductase comprising:
(a) culturing the host cell of claim 13 under conditions that allow the production of the Coenzyme A disulfide reductase; and
(b) recovering the Coenzyme A disulfide reductase.

20. A probe useful for detecting the presence of a polynucleotide encoding a CoADR, comprising an oligonucleotide of at least twenty nucleotides of any of SEQ ID Nos: 1, 10, 12, 14 or 16 or complementary sequences thereof, wherein said oligonucleotide hybridizes to RNA or DNA encoding the CoADR under the following conditions: hybridization and washing in 0.1× SSC buffer containing 0.1% SDS at 68° C.

21. The probe of claim 20 wherein the CoADR is from a Gram-positive coccus.

22. The probe of claim 21 wherein the Gram-positive coccus is *S. aureus, S. epidermidis, E. faecalis,* or *E. faecium.*

23. A method of detecting a Gram-positive coccus in a sample containing or suspected to contain the Gram-positive coccus, comprising the steps of:
(a) contacting the sample with the oligonucleotide probe of claim 21, thereby forming a hybrid complex;
(b) detecting the presence of a hybrid complex; and
(c) correlating the presence of the hybrid complex with the presence of the Gram-positive coccus in the test sample.

24. A diagnostic test kit comprising:
(a) an oligonucleotide according to claim 20; and
(b) instructions for conducting the diagnostic test.

* * * * *